(12) United States Patent
Qin et al.

(10) Patent No.: US 9,266,897 B2
(45) Date of Patent: Feb. 23, 2016

(54) DERIVATIVES OF PROTOBERBERINE BIOLOGICAL ALKALOIDS AND USE OF SAME INHIBITING ULCERATIVE COLITIS

(71) Applicant: Institute of Materia Medica, Chinese Academy of Medical Sciences, Beijing (CN)

(72) Inventors: Hailin Qin, Beijing (CN); Wenjie Wang, Beijing (CN); Zhihui Zhang, Beijing (CN); Lianqiu Wu, Beijing (CN); Anjun Deng, Beijing (CN); Jinqian Yu, Beijing (CN); Zhihong Li, Beijing (CN)

(73) Assignee: Institute of Materia Medica, Chinese Academy of Medical Sciences (CN)

( * ) Notice: Subject to any disclaimer, the term of this patent is extended or adjusted under 35 U.S.C. 154(b) by 0 days.

(21) Appl. No.: 14/354,019

(22) PCT Filed: Oct. 24, 2012

(86) PCT No.: PCT/CN2012/083454
§ 371 (c)(1),
(2) Date: Oct. 2, 2014

(87) PCT Pub. No.: WO2013/060274
PCT Pub. Date: May 2, 2013

(65) Prior Publication Data
US 2015/0031717 A1    Jan. 29, 2015

(30) Foreign Application Priority Data
Oct. 24, 2011   (CN) .......................... 2011 1 0325435

(51) Int. Cl.
*A61K 31/4741* (2006.01)
*C07D 491/22* (2006.01)
*C07D 455/03* (2006.01)
*C07D 491/04* (2006.01)
*C07D 491/147* (2006.01)

(52) U.S. Cl.
CPC ............ *C07D 491/22* (2013.01); *C07D 455/03* (2013.01); *C07D 491/04* (2013.01); *C07D 491/147* (2013.01)

(58) Field of Classification Search
USPC ................................ 514/279, 280; 546/41, 48
See application file for complete search history.

(56) References Cited

FOREIGN PATENT DOCUMENTS

CN         101153039 A     4/2008

OTHER PUBLICATIONS

Hung, T.M. et al.: Cholinesterase inhibitory activity and anti-amnesic activity of alkaloids from Corydalis turtschaninovii. J. of Ethnopharm., vol. 119, pp. 74-80, 2008.*

Cheng, Zhe et al. "8,8-Dimethyldihydroberberine with improved bioavailability and oral efficacy on obese and diabetic mouse models." *Bioorganic & Medicinal Chemistry*. vol. 18. No. 16. (2010); pp. 5915-5924.
Dosta'l, Jiri et al. "Berberine and coptisine free bases." *Journal of Molecular Structure*. vol. 687. No. 1-3. (2004): pp. 135-142.
Hu, Yuanli et al. "Comparison of total alkaloids from Coptis Root and berberine for ulcerative colitis treatment." *Pharmacology and Clinics of Chinese Materia Medica*. vol. 27. No. 5. (Oct. 15, 2011); pp. 45-48.
Jeffreys, John A.D. "Experiments on the Synthesis of Tetrahydroworenine." *Journal of the Chemical Society*. (Jan. 1, 1955);pp. 79-83. Downloaded by Institute of Materia Medica. CAMS & PUMC on Apr. 23, 2014.
Lee, Ga Eun et al. "Synthesis and structure-activity relationships of novel, substituted 5,6-dihydrodibenzo[a,g]quinolizinium P2X7 antagonists." *Bioorganic & Medicinal Chemistry Letters*. vol. 19. No. 3. (2009): pp. 954-958.
Simeon, S. et al. "The pharmacological activity of protoberberine alkaloids." *World Phytomedicines*. vol. 5. No. 4. (1990):pp. 156-163.

* cited by examiner

*Primary Examiner* — Charanjit Aulakh
(74) *Attorney, Agent, or Firm* — Mintz Levin Cohn Ferris Glovsky and Popeo, P.C.; Shovon Ashraf

(57) ABSTRACT

Disclosed are derivatives of protoberberine biological alkaloids or physiologically acceptable salts thereof produced by means of a derivative reaction of a source material of biological alkaline quaternary ammonium salts of protoberberine alkaloids, a preparation method for same and pharmaceutical uses thereof. The derivatives of protoberberine biological alkaloids or the physiologically acceptable salts thereof show activity inhibiting ulcerative colitis and can be used in the preparation of drugs for same.

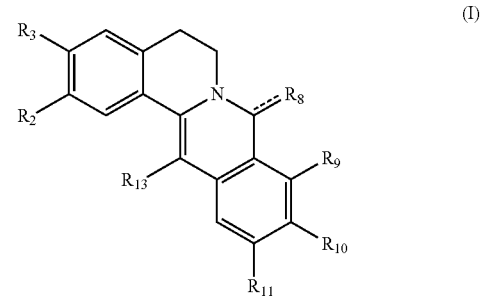

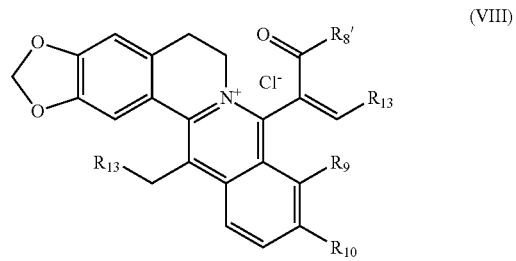

7 Claims, 5 Drawing Sheets

DERIVATIVES OF PROTOBERBERINE BIOLOGICAL ALKALOIDS AND USE OF SAME INHIBITING ULCERATIVE COLITIS

FIELD OF THE INVENTION

The present invention relates to novel protoberberine alkaloid derivatives obtained from various protoberberine alkaloids quaternium as substrate through various derivatization reactions or their physiologically acceptable salts, their preparation method and the use of them as a drug for inhibition of ulcerative colitis. The use as anti-ulcerative colitis (UC) drugs of some known protoberberine alkaloid derivatives obtained from various protoberberine alkaloids quaternium as substrate through various derivatization reactions is also involved. The specific protoberberine alkaloid derivatives or their physiologically acceptable salts are as follows: dihydrocoptisine, dihydropseudocoptisine, dihydroberberine, dihydropalmatine, 3-methyldihydrocoptisine, (±)-8-cyanodihydrocoptisine, (±)-8-cyanodihydropseudocoptisine, 8-oxodihydrocoptisine, 8-oxodihydropseudocoptisine, (±)-8-acylmethyldihydrocoptisine, 8-(1-acyl-2-alkyl-ethenyl)-13-alkylcoptisine quaternium, and 8-(1-acyl-2-alkyl-ethenyl)-13-alkylberberine quaternium. The present invention belongs to innovative drug research field.

BACKGROUND OF THE INVENTION

Inflammatory bowel disease (IBD) is a kind of chronic inflammatory disease with its etiology and pathogenesis being unclear up to now. At present, the common clinical IBD includes Crohn's disease (CD) and Ulcerative colitis (UC, also known as chronic non-specific UC), which are reported as high incidence rate, long duration, and recurrent attacks and the like. With increasing knowledge for this disease in the field of medical sciences and the development of medical diagnostic tools in recent years, clinical statistics has made it very clear that approximately 5%-7% of patients of UC will progress toward malignant transformation and probably will lead to cancerization ultimately arisen from UC, with serious dysplasia of intestinal glands and carcinoma of colon and rectum often being formed, and pathologically, the incidence of undifferentiated-type predominates in patients of UC, and too often with high degree of deterioration and poor prognosis. At present, the lack of efficient drug and other effective therapy for the treatment of UC is severe, leading to no complete cure to UC clinically. So it has been identified as nasty disease in the field of medical sciences, which seriously affected the lives of the patients. (At present, there are only several drugs, such as mesalazine (e.g. SASP etc.), immunosuppressive agents, and hormone and on the like, being used to treat UC clinically. Although some efficacy is observed, many problems abound nowadays, such as relapse after treatment and serious side effect, among others).

The lesions of UC are mainly confined to the mucosal layer of colon, too often with ulcer being the most dominant symptom and relapse after treatment and severe gastrointestinal inflammation being its characteristics, which also often implicates rectum and distal colon. These symptoms can also extend to the proximal end, and even the entire colon. According to national collaborative group of IBD, the incidence rate of UC was about 11.62 cases in 100,000 people each year in China, and hospitalized UC patients were mainly mild (35.4%) and moderate (42.9%) cases. In western countries, the morbidity of UC was 79-268 cases in 100,000 people each year, while, in Asia in the late 20th century, it was 7.8-18.1 cases and 8.6 cases in 100,000 people each year in Japan and Singapore, respectively. In recent years, morbidity of UC has shown a tendency of increasing across China (Maybe it is due to our increasing understanding for this disease and the development of medical diagnostic tools). Realistically, getting UC would make patients suffer not only from mental and physical pain, but also from heavy economic burden to themselves.

At the early stage of UC, there can be diffuse inflammation of mucosa, edema, hyperemia, and local hemorrhage, and with diffuse fine granule in the mucosal surface, fragile organization, and easy bleeding when touched also often being observed. Lymphocytes, plasma cells, eosinophils and neutrophils infiltration can be found in the mucosa and submucosa. With the progression of the disease, a large number of neutrophils will gather in the bottom of intestinal glands, leading to the formation of a small crypt abscess. When the crypt abscess are mixed together and broken up, mucosa will show wide shallow small irregular ulcer. The ulcer may develop along the longitudinal axis of colon, merging into irregular large ulcer gradually. In the process of repeated episodes of chronic colitis, a lot of new granulation tissue will proliferate, often together with inflammatory polyp. Due to the continuous damage and repair, mucosa will lose its normal structure and fibrous tissue will increase, leading to atrophic changes such as glands being degenerated, arranged in disorder, and reduced in number. With the healing of ulcer, forming of scar, and hypertrophying of muscular layer of mucosa and muscle layer, the colon will deform, colonic pouch will disappear, and even intestinal lumen will narrow, leading to the organic and functional changes of colon, which will seriously affect the health of human body.

Recent investigations have shown that the occurrence and progression of chronic IBD, including CD and UC, are closely related to an imbalance of microenvironment homeostasis function of intestinal epithelial cells. The disorder of homeostasis function of intestinal epithelial cell can trigger non-controllable endoplasmic reticulum stress response (unresolving ER stress), leading to extensive and persistent endoplasmic reticulum damage in intestinal epithelial cells, often with "programmed cell death", namely, apoptosis. Also, it has been reported that the occurrence and progression of IBD are closely related to the non-controllable endoplasmic reticulum stress response within intestinal epithelial cells. Especially the abnormality of key downstream transcription factor, X-box-binding protein 1 (xbp1), which associates with non-controllable endoplasmic reticulum stress response within intestinal epithelial cells plays a key role in the incidence of UC.

Generally, the transcription factor xbp1 plays a very important role for the expansion of endoplasmic reticulum and the growth of glandular epithelial cells sharing secretion function, such as plasma cells, islet cells in the pancreas, and salivary gland cells, and for the adaption of epithelial cells to inflammatory stimulation environment. Of almost all cell types from human body, xbp1 serve as a key regulator in maintaining the basic function of endoplasmic reticulum through directly regulating the transcriptional function of a core set of genes. Kaser and coauthors have created a gene knockout mouse model with xbp1 defect of intestinal epithelial cells (XBP1−/−) in 2008 for the first time. They found that animals with xbp1 gene knockout would generate not only the deficiency of Paneth cell and the obvious change of phenotype of goblet cell, but also the spontaneous inflammatory changes in the ileum. At the same time, further discovery was made by researchers on the basis of the above findings that the sense mutant of the xbp1 gene also related closely to the occurrence and progression of IBD. The above experimental results demonstrated that xbp1 gene plays an important role in maintaining the homeostasis of intestinal epithelial cells and in resisting the apoptosis of intestinal epithelial cell induced by ER stress. Similarly, by taking the SNPs technology in clinical studies, it was found that patients getting IBD typically show some variations in the coding region of the xbp1 gene, making them to be more sensitive to predisposing factors of IBD. Taken together, according to research data from not only clinical genetics but also in laboratories, it can be make clear that transcription factor xbp1 plays a very important role in the self homeostasis regulation of intestinal epithelial cell. The failure or weakness of xbp1 expression will increase the sensibility of body to inducing factor of IBD, promote getting IBD, and lead to deterioration of IBD.

However, there has no claim as yet to chemically synthesized small molecule drug or natural medicine monomer in the field of developing innovative anti-IBD drugs with xbp1 as target during recent research across the world. Base on the above findings from laboratory to clinical test, i.e., the research information about the close relationship between the expressive failure and abnormality of xbp1 and the increasing morbidity of IBD, it is speculated that xbp1 may be the potential new drug target for treating IBD. Therefore, the object of the present invention is to screen and discovery selective agonists of xbp1 on the basis of different aspects such as gene transcription regulation of xbp1, mRNA expression, and protein synthesis and the like by establishing drug screening model in vitro with xbp1 as target, in combination with cytology and molecular biology means, mainly including dual luciferase reporter gene, real-time quantitative polymerase chain reaction (PCR) and Western Blot (WB) techniques.

Moreover, the present invention also provides a reliable, accurate, and effective method for discovering anti-IBD drug by high-throughput screening.

The present invention obtains some protoberberine alkaloid derivatives or their physiologically acceptable salts by structure modifications of kinds of protoberberine alkaloid quaternium. In pharmacodynamic experiments at molecular and animal level, these protoberberine alkaloid derivatives show certain or significant anti-UC activity with a few of them showing far more efficiency than substrates and positive drug. Especially, the above mentioned compounds 1, 2, and 7 show significant transcriptional activation effect on xbp1 gene at molecular level in vitro, wherein the $EC_{50}$ values are $2.29 \times 10^{-9}$ (mol/L), $7.06 \times 10^{-9}$ (mol/L), and $2.21 \times 10^{-7}$ (mol/L), respectively. On the other hand, in vivo experiments show that the disease activity index (DAI) (including mental state, weight loss, bloody stool, shape of stool and other evaluation indicators) inhibitory rate of compound 7 (500 mg/kg) in UC model is up to 64%, and on the case of compound 1 (300 mg/kg) and 2 (300 mg/kg), the inhibition rates are as high as 69% and 80%, respectively, while the positive drug SASP (300 mg/kg) is only 32%. In addition, the histopathological test results show that the high-dose group of compound 7 (500 mg/kg) has significant improvement on the colon inflammatory lesion, with intestinal epithelial cells arranged perfectly, and even the cell polarity arrangement can recover to the normal physiological state. Therefore, the results from in vivo experiments of different animal species and different pathogenesis demonstrate that the protoberberine alkaloid derivatives obtained in the present invention exhibit far more significant anti-UC activity in vivo than those currently used clinically, such as SASP, and thus they have important medicinal value in preparing drugs for the treatment of UC. In addition, comparing with substrates, the solubility of these prepared protoberberine alkaloid derivatives has also been significantly improved, especially in those poor solvents for substrates.

SUMMARY OF THE INVENTION

The technical matter to be solved by the present invention is to provide a kind of drug for the treatment of UC, that is, the protoberberine alkaloid derivatives as shown in general formula I-VIII or the physiologically acceptable salts thereof.

To solve the above problem, the present invention provides the following technical solutions:

The first aspect of the present invention provides a class of protoberberine alkaloid derivatives as shown in general formula I-VIII or the physiologically acceptable salts thereof.

The second aspect of the present invention provides the preparation method of protoberberine alkaloid derivatives as shown in general formula I-VIII or the physiologically acceptable salts thereof.

The third aspect of the present invention provides the pharmaceutical composition comprising the protoberberine alkaloid derivative as shown in general formula I-VIII or the physiologically acceptable salts thereof.

The fourth aspect of the present invention provides the use of the protoberberine alkaloid derivative as shown in general formula I-VIII or the physiologically acceptable salts thereof in treatment of cancer.

The protoberberine alkaloid derivative as shown in general formula I or the pharmaceutically acceptable salts thereof comprises dihydrocoptisine, dihydroberberine, dihydropalmatine, 8-oxodihydrocoptisine, 8-oxodihydropseudocoptisine:

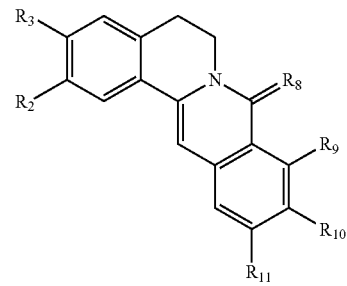

wherein:

=== represents a single bond or a double bond;

$R_2$ and $R_3$ are independently represents $OCH_3$, or $R_2$ and $R_3$ form a $OCH_2O$ together;

when === is a single bond, $R_8$ represents H; when === is a double bond, $R_8$ represents O;

$R_9$ and $R_{10}$ are independently represents $OCH_3$ with $R_{11}$ representing H, or $R_9$ and $R_{10}$ form $OCH_2O$ together with $R_{11}$ representing H, or $R_{10}$ and $R_{11}$ form $OCH_2O$ together with $R_9$ representing H.

13-Substituted dihydrocoptisine derivative as shown in the following general formula (II):

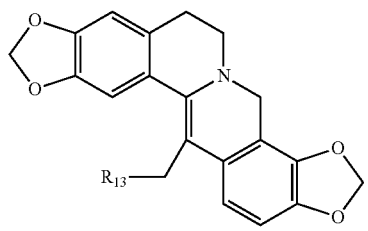

wherein:

$R_{13}$ represents H, or $R_{13}$ represents aliphatic group of formula $C_nH_{2n+1}$ or $C_mH_{2m-}$,
wherein n represents an integer between 1 and 20, and m represents an integer between 1 and 20; or $R_{13}$ is $NHR_{13}'$ wherein $R_{13}'$ is selected from H or alkyl of formula $C_nH_{2n+1}$, wherein n represents an integer between 1 and 20; or $R_{13}$ is $OR_{13}'$ wherein $R_{13}'$ is selected from H or alkyl of formula $C_nH_{2n+1}$, wherein n represents an integer between 1 and 20; or $R_{13}$ is $COOR_{13}'$ wherein $R_{13}'$ is selected from H or alkyl of formula $C_nH_{2n+1}$, wherein n represents an integer between 1 and 20; or $R_{13}$ is selected from halogen, C1-C20 alkyl sulphanyl, C1-C20 alkylacyl, or C1-C20 alkylacyloxy;

wherein the alkyl in the above aliphatic group, C1-C20 alkyl sulphanyl, C1-C20 alkylacyl, or C1-C20 alkylacyloxy is straight chain or branched chain.

Dihydropseudocoptisine and 13-substituted dihydropseudocoptisine as shown in the following general formula (III):

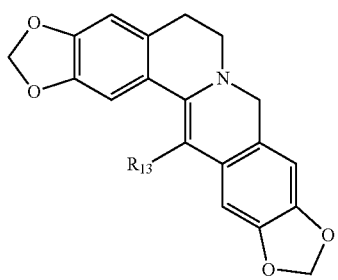

wherein:

$R_{13}$ represents H; or $R_{13}$ represents aliphatic group of formula $C_nH_{2n+1}$, wherein n represents an integer between 1 and 20; or $R_{13}$ represents aliphatic group of formula $C_mH_{2m-1}$, wherein m represents an integer between 2 and 20; or $R_{13}$ is $OR_{13}'$ wherein $R_{13}'$ is selected from H or alkyl of formula $C_nH_{2n+1}$, wherein n represents an integer between 1 and 20; or $R_{13}$ is $CH_2NHR_{13}'$ wherein $R_{13}'$ is selected from H or alkyl of formula $C_nH_{2n+1}$, wherein n represents an integer between 1 and 20; or $R_{13}$ is $CH_2OR_{13}'$ wherein $R_{13}'$ is selected from H or alkyl of formula $C_nH_{2n+1}$, wherein n represents an integer between 1 and 20; or $R_{13}$ is $CH_2COOR_{13}'$ wherein $R_{13}'$ is selected from H or alkyl of formula $C_nH_{2n+1}$, wherein n represents an integer between 1 and 20; or $R_{13}$ is $CH_2R_{13}'$ wherein $R_{13}'$ is selected from halogen, C1-C20 alkyloxy, C1-C20 alkyl sulphanyl, C1-C20 alkylacyl, or C1-C20 alkylacyloxy;

wherein the alkyl in the above aliphatic group, C1-C20 alkyloxy, C1-C20 alkyl sulphanyl, C1-C20 alkylacyl, or C1-C20 alkylacyloxy is straight chain or branched chain.

8-Substituted dihydrocoptisine and 8-substituted dihydropseudocoptisine as shown in the following general formula (IV):

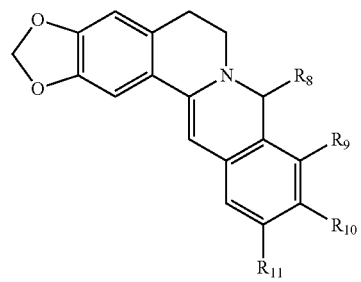

wherein:

$R_8$ represents CN; or $R_8$ is $CH_2NHR_8'$ wherein $R_8'$ is selected from H, benzyl or alkyl of formula $C_nH_{2n+1}$, wherein n represents an integer between 1 and 20; or $R_8'$ represents alkyl of formula $C_mH_{2m-1}$, wherein m represents an integer between 2 and 20; or $R_8$ is $COOR_8'$ wherein $R_8'$ is selected from H, benzyl or alkyl of formula $C_nH_{2n+1}$, wherein n represents an integer between 1 and 20; or $R_8'$ represents alkyl of formula $C_mH_{2m-1}$, wherein m represents an integer between 2 and 20;

$R_9$ and $R_{10}$ form a $OCH_2O$ together and $R_{11}$ represents H; or $R_{10}$ and $R_{11}$ form a $OCH_2O$ together and $R_9$ represents H.

(±)-8-Acylmethyl substituted dihydrocoptisine as shown in the following general formula (V):

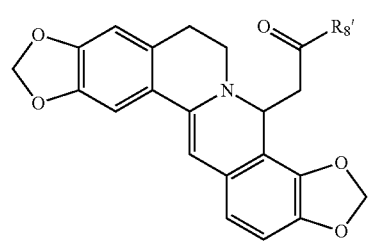

wherein:

$R_8'$ represents aliphatic group of formula $C_nH_{2n+1}$ wherein n represents an integer between 1 and 20; or $R_8'$ represents aliphatic group of formula $C_mH_{2m-1}$, wherein m represents an integer between 2 and 20; or $R_8'$ is selected from OH, $NH_2$, halogen or C1-C20 alkyloxy, C1-C20 alkyl sulphanyl;

wherein the alkyl in the above C1-C20 alkyloxy, C1-C20 alkyl sulphanyl is straight chain or branched chain.

(±)-8-Acylmethyl substituted dihydrocoptisine as shown in the following general formula (VI):

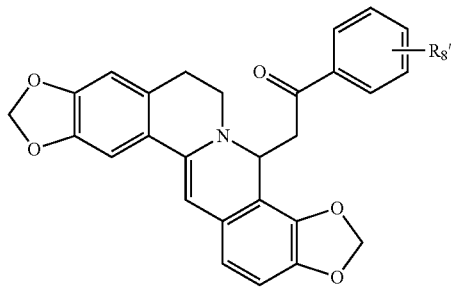

wherein:

R8' is selected from H, OH, NH₂, NO₂, phenyl, methylenedioxy, 1,2-ethylenedioxy, halogen, C1-C20 alkyl, C1-C20 alkyloxy, C1-C20 alkyl sulphanyl, C1-C20 alkylacyl, or C1-C20 alkylacyloxy; wherein the alkyl in the above C1-C20 alkyl, C1-C20 alkyloxy, C1-C20 alkyl sulphanyl, C1-C20 alkylacyl, or C1-C20 alkylacyloxy is straight chain or branched chain.

Protoberberine alkaloid quaternium as shown in the following general formula (VII), comprising 8-(1-acyl-2-alkyl-ethenyl)-13-alkylcoptisine quaternium and 8-(1-acyl-2-alkyl-ethenyl)-13-alkylberberine quaternium:

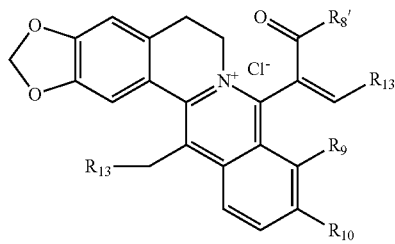

wherein:

$R_8'$ represents aliphatic group of formula $C_nH_{2n+1}$, wherein n represents an integer between 1 and 20, or $R_8'$ represents aliphatic group of formula $C_mH_{2m-1}$, wherein m represents an integer between 2 and 20; or $R_8'$ is selected from OH, NH₂, halogen, C1-C20 alkyloxy, C1-C20 alkyl sulphanyl;

wherein the alkyl in the above C1-C20 alkyloxy, C1-C20 alkyl sulphanyl is straight chain or branched chain;

$R_9$ and $R_{10}$ independently represents OCH₃, or $R_9$ and $R_{10}$ form a OCH₂O together;

$R_{13}$ is H or $R_{13}$ represents aliphatic group of formula $C_nH_{2n+1}$, wherein n represents an integer between 1 and 19.

Protoberberine alkaloid quaternium as shown in the following general formula (VIII), comprising 8-(1-acyl-2-alkyl-ethenyl)-13-alkylcoptisine quaternium and 8-(1-acyl-2-alkyl-ethenyl)-13-alkylberberine quaternium:

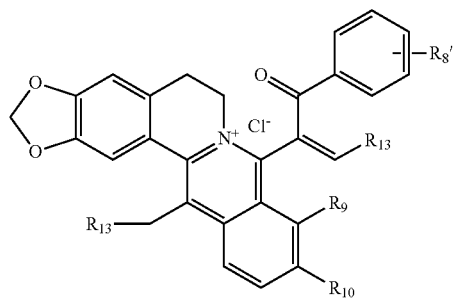

wherein:

R8' represents H, OH, NH₂, NO₂, phenyl, methylenedioxy, 1,2-ethylenedioxy, halogen, C1-C20 alkyl, C1-C20 alkyloxy, C1-C20 alkyl sulphanyl, C1-C20 alkylacyl, or C1-C20 alkylacyloxy;

wherein the alkyl in the above C1-C20 alkyl, C1-C20 alkyloxy, C1-C20 alkyl sulphanyl, C1-C20 alkylacyl, or C1-C20 alkylacyloxy is straight chain or branched chain;

$R_9$ and $R_{10}$ independently represents OCH₃, or $R_9$ and $R_{10}$ form a OCH₂O together;

$R_{13}$ is H or $R_{13}$ represents aliphatic group of formula $C_nH_{2n+1}$, wherein n represents an integer between 1 and 19.

The most preferred compounds of the present invention are selected from the group consist of compounds 1-29:

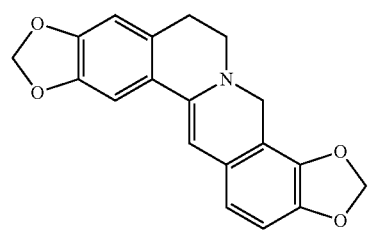

1

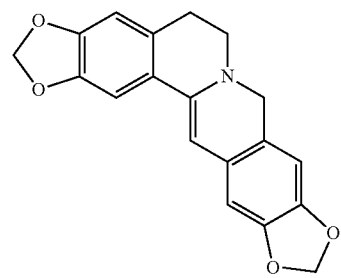

2

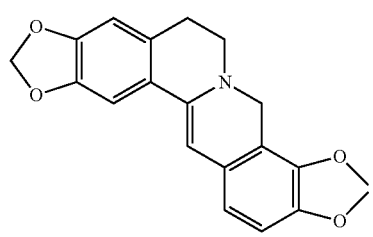

3

4
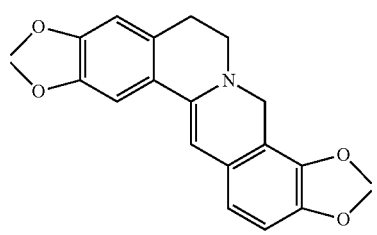
5
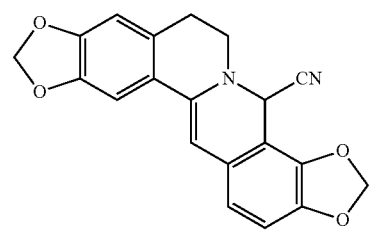
6
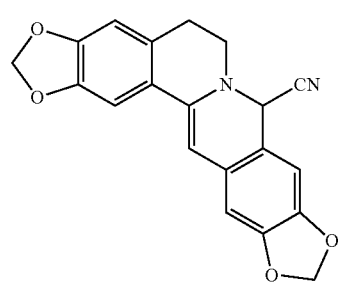
7
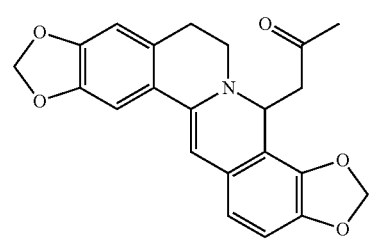
8
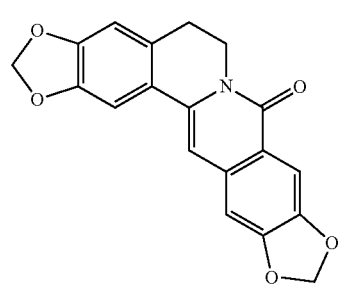
9
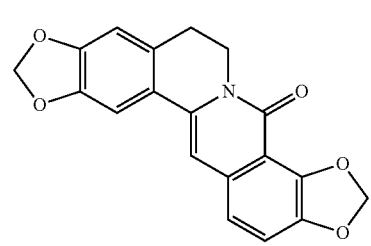
10
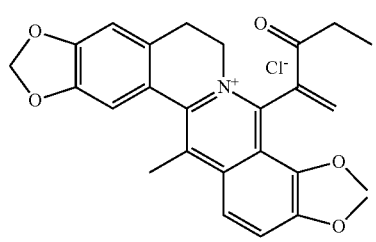
11
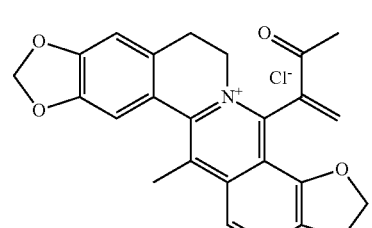
12
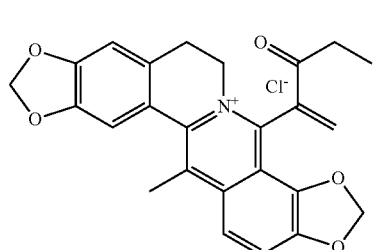
13
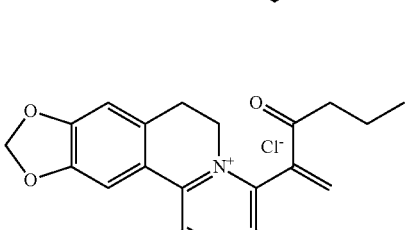
14
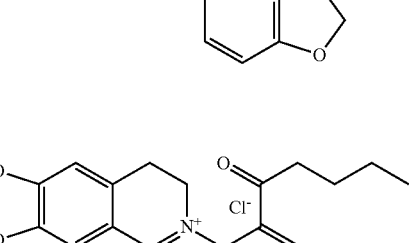
15
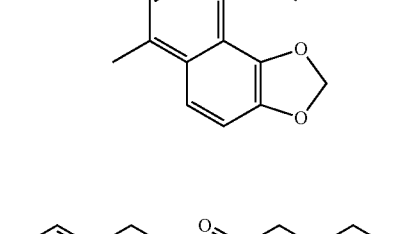

16
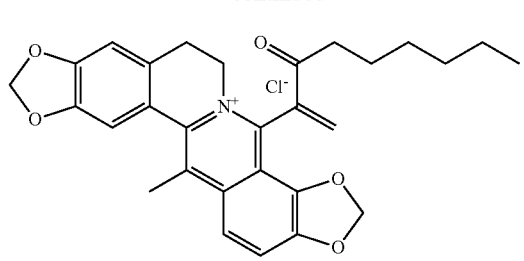
17
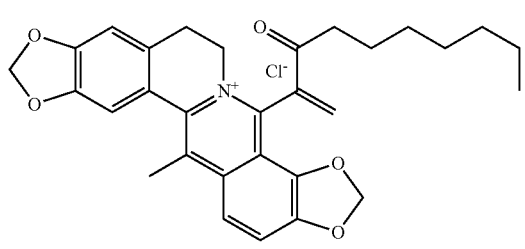
18
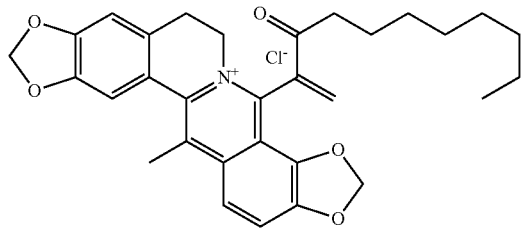
19
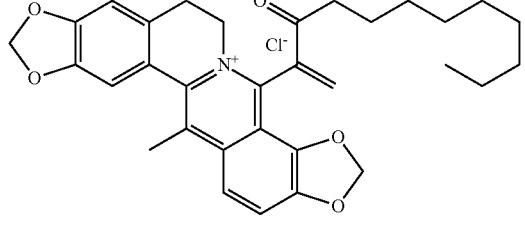
20
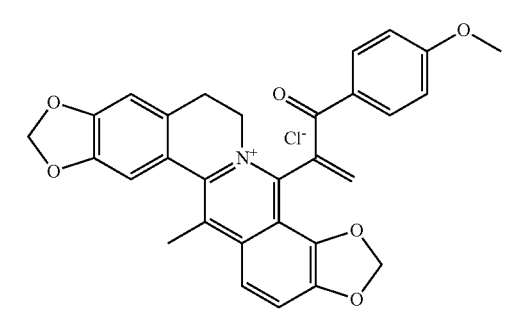
21
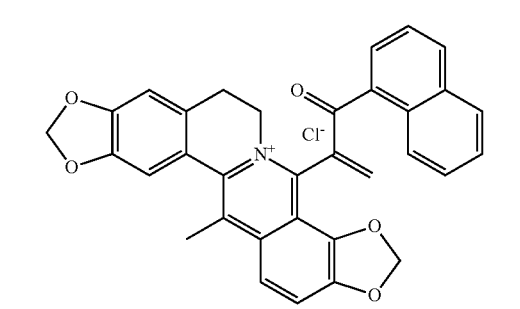
22
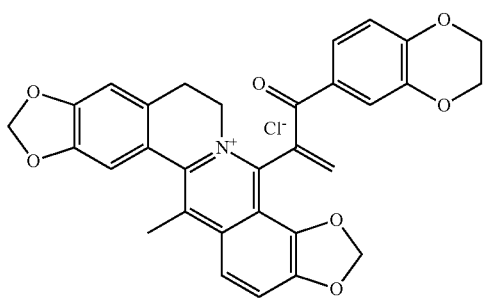
23
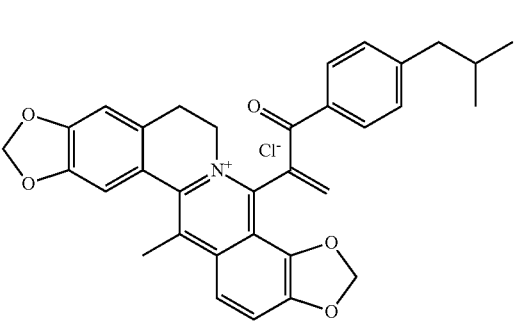
24
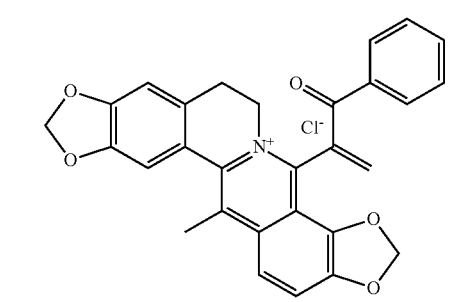
25
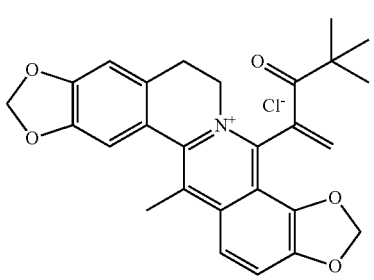
26
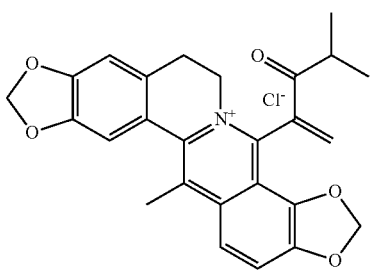

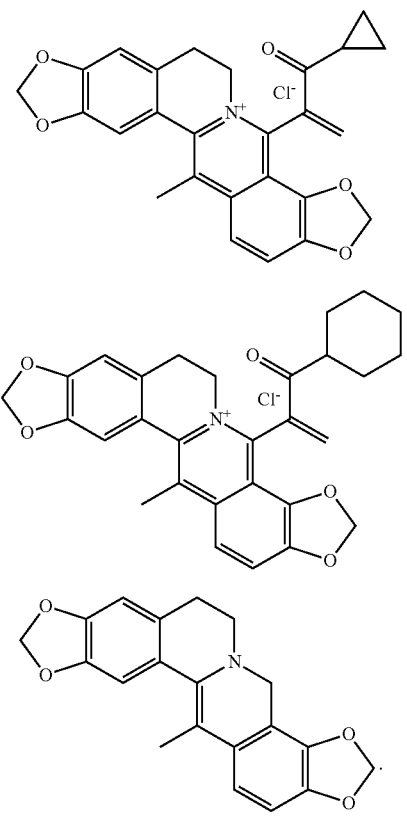

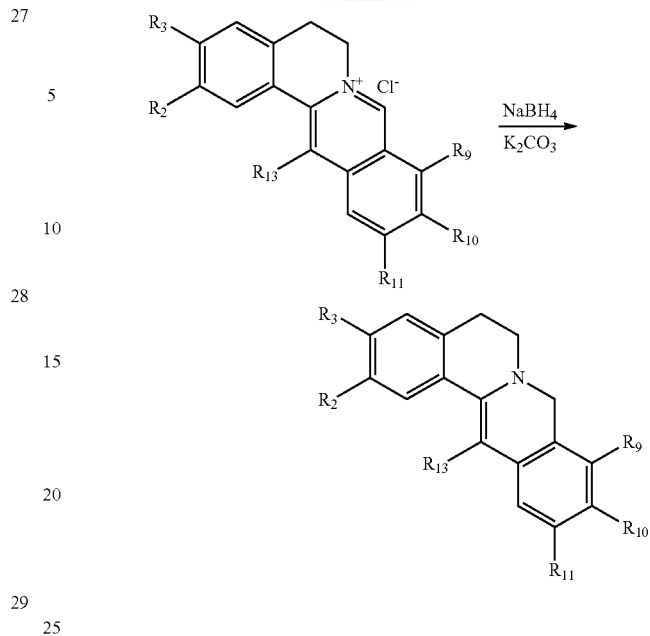

The second aspect of the present invention provides the preparation methods of the present compounds. Said protoberberine alkaloid derivatives or their physiologically acceptable salts can be synthesized, respectively, by the following synthetic methods:

(1) Dihydrocoptisine, dihydropseudocoptisine, dihydroberberine, dihydropalmatine, and 13-methyldihydrocoptisine of the present invention can be synthesized by the following synthetic method:

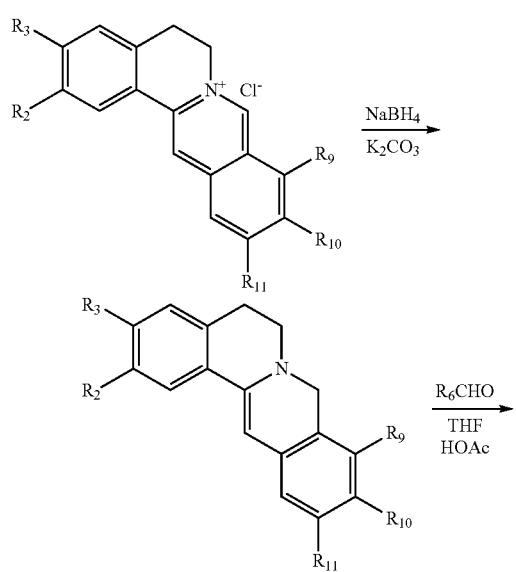

(2) (±)-8-Cyanodihydrocoptisine and (±)-8-cyanodihydropseudocoptisine of the present invention can be synthesized by the following synthetic method:

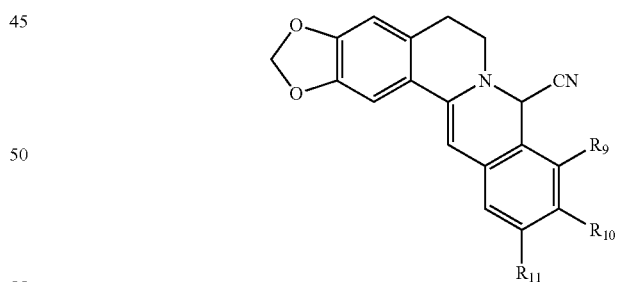

(3) 8-Oxodihydropseudocoptisine of the present invention can be synthesized by the following synthetic method:

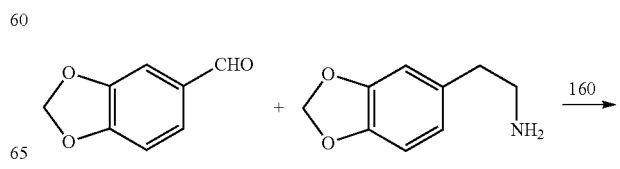

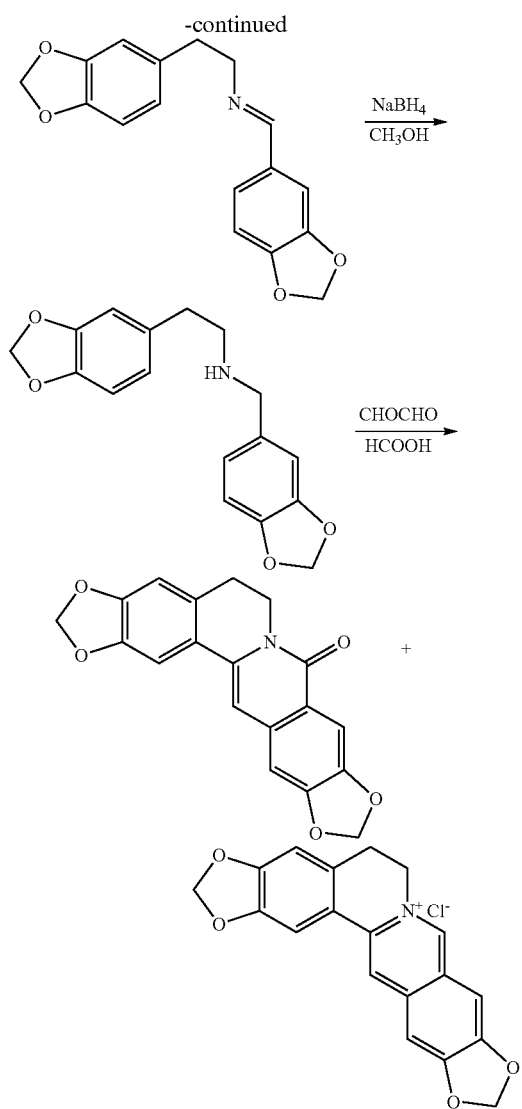

(4) 8-Oxodihydrocoptisine of the present invention can be synthesized by the following synthetic method:

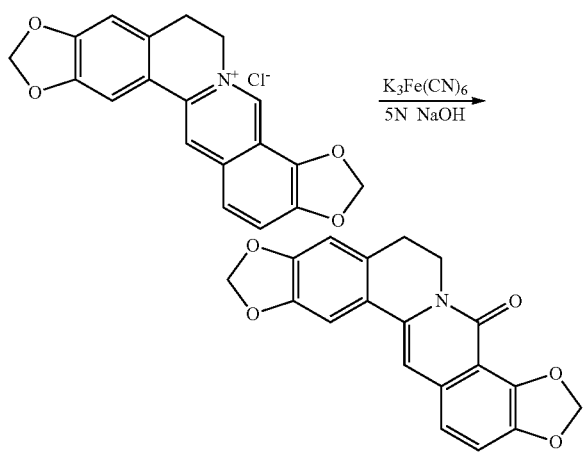

(5) (±)-8-Acylmethyl substituted dihydrocoptisine, 8-(1-acyl-2-alkyl-ethenyl)-13-alkylcoptisine quaternium and 8-(1-acyl-2-alkyl-ethenyl)-13-alkylberberine quaternium of the present invention can be synthesized by the following synthetic method:

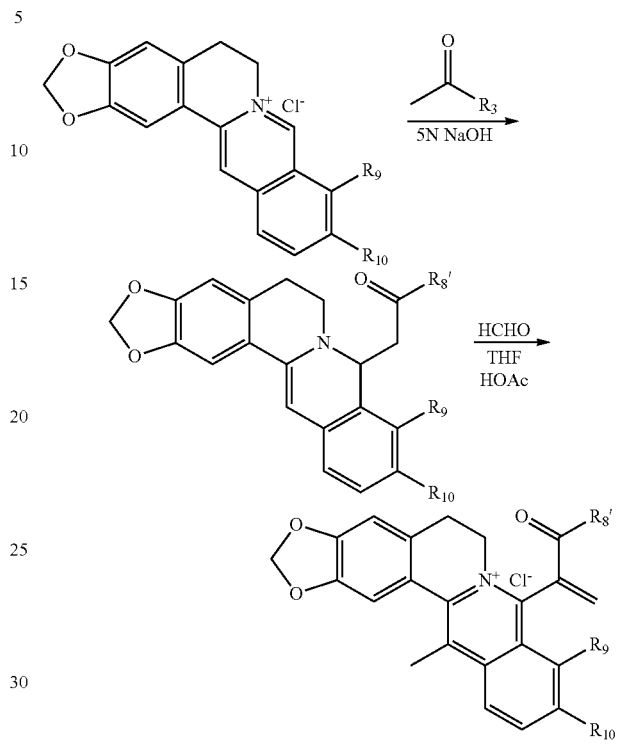

The third aspect of the present invention also relates to the pharmaceutical compositions comprising the present compounds as active ingredients. Methods for preparing said pharmaceutical compositions will be readily apparent to those skilled in the art. The present compounds can be combined with one or more pharmaceutically acceptable solid or liquid excipient and/or adjuvant to form any dosage form suitable for human or animal use. Generally, the pharmaceutical composition will comprise from 0.1 wt % to 95 wt % of the present compounds.

The present invention compounds or its pharmaceutical compositions may be administered intestinally or parenterally in unit dosage form, for example, oral, intravenous, intramuscular, subcutaneous, nasal, oral mucosa, ocular, lung, respiratory tract, skin, vagina, rectum etc.

The dosage form may be liquid, solid or semi-solid formulation. Liquid formulation may be, for example, solution (including true solution and colloid solution), emulsions (including o/w type, w/o type and multiple emulsions), suspensions, injections (including aqueous injections, powder and infusion), eye drops, nasal drops, lotions and liniments, etc.; solid formulation may be, for example, tablets (including conventional tablets, enteric-coate tablets, lozenges, dispersible tablets, chewable tablets, effervescent tablets, orally disintegrating tablets), capsules (including hard capsules, soft capsules, enteric capsules), granules, powders, pellets, pills, suppositories, films, patches, gas (powder) aerosols, sprays, etc.; semi-solid formulation may be, for example, ointments, gels, pastes, etc.

The present compounds may be formulated into general preparations, also sustained release preparations, controlled-release preparations, targeting preparations and particulate delivery systems.

Tablets can be prepared by mixing the present compounds with various widely used excipients what is known in the art, including diluents, binders, wetting agents, disintegrants, lubricants, glidants. Diluents may be starch, dextrin, sucrose, glucose, lactose, mannitol, sorbitol, xylitol, microcrystalline cellulose, calcium sulfate, calcium hydrogen phosphate, calcium carbonate, etc.; wetting agents may be water, ethanol, isopropanol, etc.; binder may be starch, dextrin, syrup, honey, glucose solution, microcrystalline cellulose, arabic gum, gelatin, sodium carboxymethyl cellulose, methyl cellulose, hydroxypropylmethyl cellulose, ethyl cellulose, acrylic resins, carbomer, polyvinyl pyrrolidone, polyethylene glycol, etc.; disintegrants may be dry starch, microcrystalline cellulose, low substituted hydroxypropyl cellulose, cross-linked poly vinyl pyrrolidone, cross-linked sodium carboxymethyl cellulose, sodium carboxymethyl starch, sodium bicarbonate and citric acid, polyoxyethylene sorbitan fatty acid esters, sodium lauryl sulfate, etc.; lubricants and glidants may be talc, silicon dioxide, stearate, tartaric acid, liquid paraffin, polyethylene glycol, etc.

Tablets may be further treated with suitable coating materials, for example, sugar-coated tablets, film-coated tablets, enteric coated tablets, or double tablets and multilayer tablets.

In order to prepare capsules, the present compounds may be mixed with diluents, glidants and the mixture is directly placed into hard or soft capsules. The present compounds may also be formulated into granules or pellets with diluents, binders, and disintegrants, and then placed into hard or soft capsules. The diluents, binders, wetting agents, disintegrants, glidants which are used in the preparation of tablets can also be used to prepare capsules of the present compounds.

The present compounds may be formulated into injection, using water, ethanol, isopropanol, propylene glycol or their mixture as solvents, and adding an appropriate amount of solubilizers, cosolvents, pH modifiers, osmo-regulators widely used in this field. Solubilizers or cosolvents may be poloxamer, lecithin, hydroxypropyl-β-cyclodextrin etc.; pH modifiers may be phosphate, acetate, hydrochloric acid, sodium hydroxide, etc.; osmo-regulators may be sodium chloride, mannitol, glucose, phosphate, acetate, etc. For the preparation of freeze-dried powder injection, proppants such as mannitol, glucose and the like may be added.

Moreover, if necessary, the pharmaceutical formulations may be added with colourants, preservatives, fragrances, flavorants or other additives.

To achieve the purpose of the medication, enhance the therapeutic effect, the present compounds or pharmaceutical compositions can be administered via any known route.

The dosage of the pharmaceutical compositions may vary in a wide range according to the nature and severity of the disease, the individual circumstances of the patient or animal, route of administration and the dosage form. In general, the suitable daily dose of the present compounds is 0.001-150 mg/Kg body weight, preferably 0.1-100 mg/Kg body weight, more preferably 1-60 mg/Kg body weight, most preferably 2-30 mg/Kg body weight. The above mentioned dosage may be administered at one dosage unit or several dosage units, depending on the doctor's clinical experience and therapeutic regimens including other means.

The present compounds or pharmaceutical compositions may be administered alone or in combination with other therapeutic or symptomatic drugs. When there is a synergistic effect between the present compounds and other therapeutic agents, the dose should be adjusted according to actual situation.

In the fourth aspect, the present invention provides the application of the compounds in the preparation of drugs for the treatment of UC. In activity test experiments at molecular and animal levels, the protoberberine alkaloid derivatives and their physiologically acceptable salts involved in the present invention show significant or certain anti-UC activity with a few of them showing far more efficacy than substrates and positive drug, and thus they have important medicinal value in the treatment of UC. Especially, the above mentioned compounds 1, 2, and 7 show significant transcriptional activation effect on xbp1 gene in vitro, wherein the $EC_{50}$ values are $2.29 \times 10^{-9}$ (mol/L), $7.06 \times 10^{-9}$ (mol/L), and $2.21 \times 10^{-7}$ (mol/L), respectively. On the other hand, animal experiments in vivo show that, the disease activity index (DAI) (including mental state, weight loss, bloody stool, shape of stool and other aspects of evaluation) inhibitory rate of compound 7 (500 mg/kg) in UC model is up to 64%, and on the case of compound 1 (300 mg/kg) and 2 (300 mg/kg), the inhibition rates are as high as 69% and 80%, respectively, while the positive drug SASP (300 mg/kg) is only 32%. In addition, the histopathological test results show that the high-dose group of compound 7 (500 mg/kg) has significant improvement on the inflammatory lesion, with intestinal epithelial cells arranged perfectly, and even the cell polarity arrangement can recover to the normal physiological state. Therefore, the results from in vivo experiments of different animal species and different pathogenesis demonstrate that the protoberberine alkaloid derivatives obtained in the present invention exhibit far more significant anti-UC activity in vivo than those currently used clinically, such as SASP, and thus they have important medicinal value in preparing drugs for the treatment of UC. In addition, comparing with substrates, the solubility of these prepared protoberberine alkaloid derivatives has also been significantly improved, especially in those poor solvents of substrates.

DETAILED DESCRIPTION OF THE INVENTION

Preparation Example 1

Figure 1:
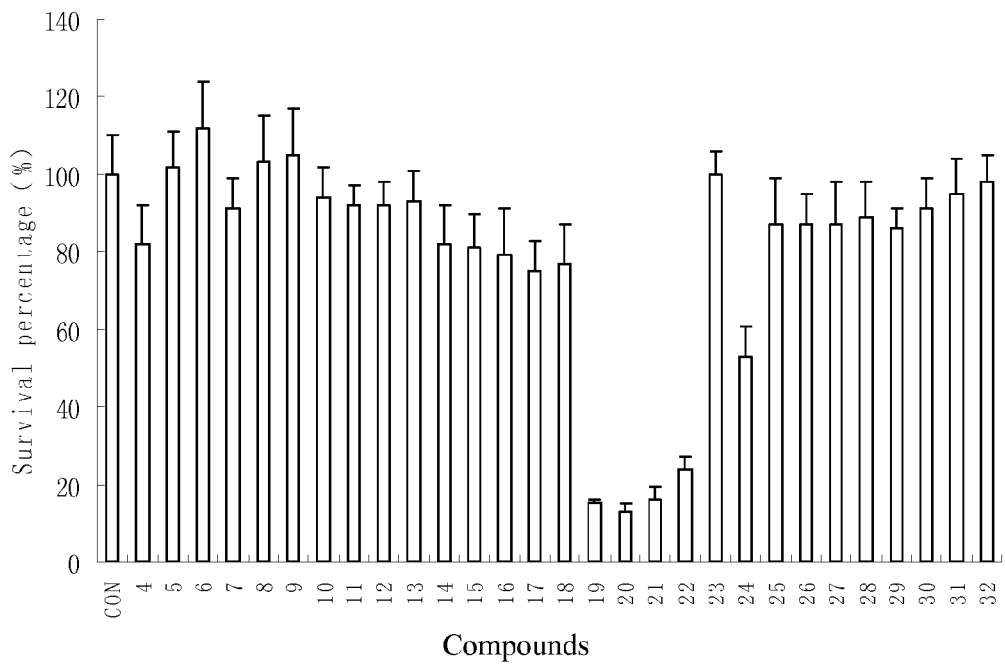
FIG. 1 shows the results of toxicity test of each compound for intestinal epithelial cells IEC-6 determined by MTT assay in vitro.

Preparation Process of Compounds 1-29 and their Structural Identification Data

Preparation of Compound 1

To a stirred solution of coptisine (102 mg, 0.29 mmol) and $K_2CO_3$ (110 mg, 0.80 mmol) in methanol (4 mL), 5% NaOH solution (0.8 mL) containing NaBH$_4$ (9 mg, 0.24 mmol) was added dropwise in ice bath. After addition, the ice bath was removed and the reaction mixture was stirred continually at room temperature for 3 h until the reaction completed. The precipitated product was filtered, washed with 30% ethanol (5 mL) and 80% ethanol (3 mL) and then recrystallized from ethanol to provide yellow solid (59 mg, 64.1% yield).

$^1$H-NMR (DMSO-d$_6$) δ (ppm): 2.78 (t, J=5.7 Hz, 2H, NCH$_2$CH$_2$), 3.04 (t, J=5.7 Hz, 2H, NCH$_2$CH$_2$), 4.15 (s, 2H, NCH$_2$), 5.96 (s, 2H, OCH$_2$O), 5.99 (s, 2H, OCH$_2$O), 6.08 (s, 1H, ArH), 6.46 (d, J=7.8 Hz, 1H, ArH), 6.68 (d, J=7.8 Hz, 1H, ArH), 6.74 (s, 1H, ArH), 7.28 (s, 1H, ArH). MS (m/z): 321.3.

Preparation of Compound 2

To a stirred solution of pseudocoptisine (310 mg, 0.87 mmol) and K$_2$CO$_3$ (300 mg, 2.17 mmol) in methanol (8 mL), 5% NaOH solution (1.5 mL) containing NaBH$_4$ (33 mg, 0.87 mmol) was added dropwise. The reaction mixture was stirred at room temperature for 3 h until the reaction completed and the precipitated product was filtered, washed to neutral with water and then dried to provide yellow solid (222 mg, 79.3% yield).

$^1$H-NMR (DMSO-d$_6$) δ (ppm): 2.78 (t, J=5.7 Hz, 2H, NCH$_2$CH$_2$), 3.00 (t, J=5.7 Hz, 2H, NCH$_2$CH$_2$), 4.06 (s, 2H, NCH$_2$Ar), 5.91 (s, 2H, OCH$_2$O), 5.99 (s, 2H, OCH$_2$O), 6.04 (s, 1H, ArH), 6.57 (s, 1H, ArH), 6.70 (s, 1H, ArH), 6.75 (s, 1H, ArH), 7.26 (s, 1H, ArH).

Preparation of Compound 3

To a stirred solution of berberine (810 mg, 2.18 mmol) and K$_2$CO$_3$ (753 mg, 5.45 mmol) in methanol (8 mL), 5% NaOH solution (1.5 mL) containing NaBH$_4$ (83 mg, 2.19 mmol) was added dropwise. The reaction mixture was stirred at room temperature for 3 h until the reaction completed and the precipitated product was filtered, washed to neutral with water and then dried to provide yellow solid (619 mg, 84.2% yield).

$^1$H-NMR (CDCl$_3$) δ (ppm): 2.78 (t, J=5.7 Hz, 2H, NCH$_2$CH$_2$), 3.04 (t, J=5.7 Hz, 2H, NCH$_2$CH$_2$), 3.70 (s, 3H, OCH$_3$), 3.75 (s, 3H, OCH$_3$), 4.20 (s, 2H, NCH$_2$Ar), 5.99 (s, 2H, OCH$_2$O), 6.04 (s, 1H, ArH), 6.68 (d, J=8.4 Hz, 1H, ArH), 6.74 (s, 1H, ArH), 6.81 (d, J=8.7 Hz, 1H, ArH), 7.28 (s, 1H, ArH).

Preparation of Compound 4

To a stirred solution of palmatine (82 mg, 0.21 mmol) and K$_2$CO$_3$ (72 mg, 0.52 mmol) in methanol (5 mL), 5% NaOH solution (0.5 mL) containing NaBH$_4$ (8 mg, 0.21 mmol) was added dropwise. The reaction mixture was stirred at room temperature for 3 h until the reaction completed and the precipitated product was filtered, washed to neutral with water and then dried to provide yellow solid (59 mg, 79.0% yield).

$^1$H-NMR (CDCl$_3$) δ (ppm): 2.91 (t, J=5.4 Hz, 2H, NCH$_2$CH$_2$), 3.16 (t, J=5.4 Hz, 2H, NCH$_2$CH$_2$), 3.85 (s, 6H, 2OCH$_3$), 3.89 (s, 3H, OCH$_3$), 3.94 (s, 3H, OCH$_3$), 4.33 (s, 2H, NCH$_2$Ar), 6.00 (s, 1H, ArH), 6.60 (s, 1H, ArH), 6.75 (s, 1H, ArH), 7.18 (s, 1H, ArH).

Preparation of Compound 5

Coptisine (300 mg, 0.84 mmol) was dissolved in methanol (8 mL), water solution (1 mL) containing KCN (55 mg, 0.84 mmol) was added dropwise. The reaction mixture was stirred at room temperature for 2 h until the reaction completed. Then, the reaction mixture was filtered and the filter cake was washed with water and then dried to provide yellow solid (230 mg, 79.0% yield).

$^1$H-NMR (DMSO-d$_6$) δ (ppm): 2.79-2.84 (m, 2H, NCH$_2$CH$_2$), 3.05-3.15 (m, 1H, NCH$_2$CH$_2$), 3.44-3.48 (m, 1H, NCH$_2$CH$_2$), 6.01 (s, 2H, OCH$_2$O), 6.03 (d, J=3.6 Hz, 2H, OCH$_2$O), 6.17 (s, 1H, CHCN), 6.41 (s, 1H, ArH), 6.66 (d, J=7.8 Hz, 1H, ArH), 6.79 (s, 1H, ArH), 6.90 (d, J=8.1 Hz, 1H, ArH), 7.36 (s, 1H, ArH).

Preparation of Compound 6

Pseudocoptisine (37 mg, 0.10 mmol) was dissolved in methanol (3 mL), and water solution (0.5 mL) containing KCN (7 mg, 0.11 mmol) was added dropwise. The reaction mixture was stirred at room temperature for 2 h until the reaction completed. Then, the reaction mixture was filtered and the filter cake was washed with water and then dried to provide yellow solid (9 mg, 25.0% yield).

$^1$H-NMR (DMSO-d$_6$) δ (ppm): 2.86 (br s, 2H, NCH$_2$CH$_2$), 3.15-3.35 (m, 2H, NCH$_2$CH$_2$), 5.80 (s, 1H, CHCN), 6.01-6.03 (m, 4H, OCH$_2$O), 6.36 (s, 1H, ArH), 6.75 (s, 1H, ArH), 6.80 (s, 1H, ArH), 6.93 (s, 1H, ArH), 7.34 (s, 1H, ArH).

Preparation of Compound 7

To a stirred solution of coptisine (99 mg, 0.28 mmol) in 5N NaOH (1.5 ml), acetone (0.2 mL, 2.7 mmol) was added dropwise. The reaction mixture was stirred at room temperature for 1 h until the reaction completed. The reaction mixture was filtered and the filter cake was washed to neutral with water, and then recrystallized from acetone to provide yellow solid (59 mg, 56.2% yield).

$^1$H-NMR (DMSO-d$_6$) δ (ppm): 2.01 (s, 3H, CHCH$_2$COCH$_3$), 2.43-2.49 (m, 1H, CHCH$_2$COCH$_3$), 2.68-2.75 (m, 2H, NCH$_2$CHH$_2$), 2.91 (dd, J$_1$=14.4 Hz, J$_2$=5.7 Hz, 1H, CHCH$_2$COCH$_3$), 3.17-3.23 (m, 2H, NCH$_2$CH$_2$), 5.08 (t, J=5.7 Hz, 1H, CHCH$_2$COCH$_3$), 5.89 (s, 1H, ArCH=C), 5.96-6.02 (m, 4H, 2OCH$_2$O), 6.49 (d, J=7.8 Hz, 1H, ArH), 6.71 (d, J=7.8 Hz, 1H, ArH), 6.75 (s, 1H, ArH), 7.24 (s, 1H, ArH). MS (m/z): 337.2.

Preparation of Compound 8

A stirred mixture of heliotropin (411 mg, 2.74 mmol) and homopiperony lamine (0.5 mL, 3.04 mmol) was heated at 160° C. for 1 h. Then, the temperature was allowed to fall to 80° C. and CH$_3$OH (6 mL) was added. When the temperature returned to room temperature, NaBH$_4$ (125 mg, 3.30 mmol) was slowly added portion wise and the mixture was refluxed for an additional 1 h, then cooled to room temperature, and poured into water (10 mL). The aqueous phase was extracted with CHCl$_3$ and the organic layer was washed with brine, and dried over anhydrous MgSO$_4$ and then filtered. Concentration of the organic layer in vacuo followed by purification of the residue by column chromatography (silica gel, CHCl$_3$/CH$_3$OH (v/v), 100:1) gave yellow oil as an intermediate product (795 mg, 97.0% yield).

$^1$H-NMR (DMSO-d$_6$) δ (ppm): 2.86-2.91 (m, 2H, NCH$_2$CH$_2$), 2.99-3.05 (m, 2H, NCH$_2$CH$_2$), 4.04 (s, 2H, NCH$_2$Ar), 5.97 (s, 2H, OCH$_2$O), 6.04 (s, 2H, OCH$_2$O), 6.68 (dd, J$_1$=8.1 Hz, J$_2$=1.5 Hz, 1H, ArH), 6.82 (s, 1H, ArH), 6.84 (d, J=8.1 Hz, 1H, ArH), 6.94 (d, J=8.1 Hz, 1H, ArH), 7.00 (dd, J$_1$=8.1 Hz, J$_2$=1.5 Hz, 1H, ArH), 7.16 (d, J=1.5 Hz, 1H, ArH).

Anhydrous CuSO$_4$ (4.2 g, 26.32 mmol) was dissolved in formic acid (15 mL) in reaction flask and maintained in 50° C. oil bath for 30 min to dehydration. The above obtained yellow oil (3.987 g, 13.32 mmol) and glyoxal (3.4 mL, 26.71 mmol) were added and the reaction mixture was heated to 100° C. and stirred for 4 h. During the reaction, concentrated hydrochloric acid was added in following order: 0.3 mL of con. HCl was added when the thermal preservation was up to 45 min; 0.3 mL was added when it was up to 90 min; 0.4 mL was added when it was up to 150 min; 0.4 mL was added when it was up to 210 min; and then 0.3 mL was added when it was up to 230 min. When the addition was completed, the reaction was carried on for 10 min, and then allowed to cool down to 10° C. to freeze for 1 h. The reaction mixture was filtered and the filter cake was dried and then recrystallized from DMF to provide pseudocoptisine (1.15 g, 24.3% yield) and recrystallized from 80% $CH_3OH$ to provide compound 8 (718 mg, 16.1% yield).

$^1$H-NMR (DMSO-$d_6$) δ (ppm): 3.01 (t, J=5.7 Hz, 2H, $NCH_2CH_2$), 4.53 (t, J=5.7 Hz, 2H, $NCH_2CH_2$), 6.04 (s, 2H, $OCH_2O$), 6.26 (s, 2H, $OCH_2O$), 6.92 (s, 1H, ArH), 7.39 (s, 1H, ArH), 7.67 (s, 1H, ArH), 8.40 (s, 1H, ArH), 8.58 (s, 1H, ArH).

Preparation of Compound 9

Potassium ferricyanide (2.2 g, 6.68 mmol) was dissolved in the solution of 5N NaOH (5 mL) followed by addition of coptisine (500 mg, 1.41 mmol). The mixture was refluxed for 10 h until the reaction completed, and then allowed to return to room temperature. The reaction mixture was filtered and filter cake was washed with water to neural and then dried to give yellow solid (344 mg, 73.0% yield).

$^1$H-NMR (DMSO-$d_6$) δ: 2.86 (t, J=5.4 Hz, 2H, $NCH_2CH_2$), 4.09 (t, J=5.4 Hz, 2H, $NCH_2CH_2$), 6.07 (s, 2H, $OCH_2O$), 6.19 (s, 2H, $OCH_2O$), 6.92 (s, 1H, ArH), 7.11 (s, 1H, ArH), 7.15 (d, J=8.1 Hz, 1H, ArH), 7.34 (d, J=8.1 Hz, 1H, ArH), 7.47 (s, 1H, ArH).

Preparation of Compound 10

To a stirred solution of berberine (95 mg, 0.26 mmol) in 5N NaOH (1 ml), butanone (0.3 mL, 3.35 mmol) was added dropwise. After addition, the reaction mixture was heated to 60° C. for 3 h and then the reaction mixture was extracted with $CHCl_3$/MeOH (v/v=10:1). The organic layer was washed to neutral with water, dried over anhydrous $MgSO_4$ and then filtered and concentrated under reduced pressure to give crude product. The crude product was dissolved in anhydrous tetrahydrofuran (3 mL) followed by addition of HOAc (0.5 mL) and formaldehyde (0.6 mL, 6.02 mmol) dropwise. The reaction mixture was refluxed for 3 h. After the reaction completed, the reaction mixture was concentrated and added with 2 N HCl (2 mL), then stirred at room temperature for 1 h and extracted with $CHCl_3$/MeOH (v/v=10:1). The organic layer was dried over anhydrous $MgSO_4$ and then filtered and concentrated under reduced pressure to give crude product, which was purified via silica gel column chromatography ($CHCl_3$/MeOH (v/v)=20:1) to give pure yellow solid (35 mg, 28.8% yield).

$^1$H-NMR (DMSO-$d_6$) δ (ppm): 0.86 (t, J=6.9 Hz, 3H, $CH_2CH_3$), 2.42 (q, J=7.2 Hz, 2H, $CH_2CH_3$), 3.15 (s, 3H, $ArCH_3$), 2.94-3.11 (m, 2H, $NCH_2CH_2$), 3.84 (s, 3H, $OCH_3$), 3.88 (s, 3H, $OCH_3$), 3.97-4.01 (m, 1H, $NCH_2CH_2$), 4.41-4.44 (m, 1H, $NCH_2CH_2$), 6.03 (s, 1H, ArH), 6.26 (d, J=4.5 Hz, 2H, $OCH_2O$), 6.67 (s, 1H, ArH), 7.23 (s, 1H, C=$CH_2$), 7.28 (d, J=9.0 Hz, 1H, ArH), 7.43 (s, 1H, C=$CH_2$), 7.52 (d, J=8.4 Hz, 1H, ArH).

Preparation of Compound 11

To a stirred solution of (±)-8-acetonyldihydrocoptisine (205 mg, 0.54 mmol) in anhydrous tetrahydrofuran (4 mL), HOAc (2 mL) and formaldehyde (1 mL, 10.04 mmol) was added dropwise. The reaction mixture was refluxed for 5 h. After the reaction completed, the reaction mixture was concentrated and added with 2 N HCl (2 mL), then stirred at room temperature for 1 h and extracted with $CHCl_3$/MeOH (v/v=10:1). The organic layer was dried over anhydrous $MgSO_4$ and then filtered and then concentrated under reduced pressure to give crude product, which was purified via silica gel column chromatography ($CHCl_3$/MeOH (v/v)=20:1) to give pure yellow solid (170 mg, 71.5% yield).

$^1$H-NMR (DMSO-$d_6$) δ: 2.60 (s, 3H, $COCH_3$), 2.91 (s, 3H, $ArCH_3$), 2.91-3.09 (m, 2H, $NCH_2CH_2$), 4.39-4.48 (m, 2H, $NCH_2CH_2$), 6.16 (s, 2H, $OCH_2O$), 6.35 (d, J=10.5 Hz, 2H, $OCH_2O$), 6.81 (s, 1H, C=$CH_2$), 7.15 (s, 1H, ArH), 7.16 (s, 1H, C=$CH_2$), 7.40 (s, 1H, ArH), 8.03 (m, 2H, ArH). MS (m/z): 402.1 [M-Cl]$^+$.

Preparation of Compound 12

To a stirred solution of coptisine (105 mg, 0.30 mmol) in 5 N NaOH (1 ml), butanone (0.3 mL, 3.35 mmol) was added dropwise. The reaction mixture was stirred at 60° C. for 3 h and then the mixture was extracted with $CHCl_3$/MeOH (v/v=10:1). The organic layer was washed to neutral with water, and dried over anhydrous $MgSO_4$, and filtered, and then concentrated under reduced pressure to give intermediate product. The intermediate product was dissolved in anhydrous tetrahydrofuran (3 mL) followed by addition of HOAc (0.5 mL) and formaldehyde (0.6 mL, 6.02 mmol) dropwise. The reaction mixture was kept refluxing for 3 h. After the reaction completed, the reaction mixture was concentrated and added with 2 N HCl (2 mL), then stirred at room temperature for 1 h and extracted with $CHCl_3$/MeOH (v/v=10:1). The organic layer was dried over anhydrous $MgSO_4$ and then filtered and concentrated under reduced pressure to give crude product, which was purified via silica gel column chromatography ($CHCl_3$/MeOH(v/v)=20:1) to give pure yellow solid (43 mg, 32.3% yield).

$^1$H-NMR ($CDCl_3$) δ: 1.16 (t, J=7.2 Hz, 3H, $CH_2CH_3$), 2.90 (s, 3H, $ArCH_3$), 3.05 (q, J=7.2 Hz, 2H, $CH_2CH_3$), 3.13-3.32 (m, 2H, $NCH_2CH_2$), 4.27-4.34 (m, 1H, $NCH_2CH_2$), 4.90-4.98 (m, 1H, $NCH_2CH_2$), 6.05 (d, J=2.1 Hz, 2H, $OCH_2O$), 6.18 (s, 1H, $OCH_2O$), 6.27 (s, 1H, $OCH_2O$), 6.83 (s, 1H, ArH), 7.04 (s, 1H, ArH), 7.17 (s, 1H, C=$CH_2$), 7.24 (s, 1H, C=$CH_2$), 7.67 (d, J=9.0 Hz, 1H, ArH), 7.80 (d, J=9.0 Hz, 1H, ArH). MS (m/z): 416.1 [M-Cl]$^+$.

Preparation of Compound 13

To a stirred solution of coptisine (300 mg, 0.84 mmol) in 5 N NaOH (1.5 ml), 2-pentanone (0.8 mL, 7.52 mmol) was added dropwise. The reaction mixture was stirred at 60° C. for 3 h. The reaction mixture was extracted with $CHCl_3$/MeOH (v/v=10:1). The organic layer was washed to neutral with water, and dried over anhydrous $MgSO_4$, and filtered, and then concentrated under reduced pressure to give intermediate product. The intermediate product was dissolved in anhydrous tetrahydrofuran (5 mL) followed by addition of HOAc (1 mL) and formaldehyde (1.5 mL, 15.06 mmol) dropwise. The reaction mixture was kept refluxing for 3 h. After the reaction completed, the reaction mixture was concentrated and added with 2 N HCl (2 mL), then stirred at room temperature for 1 h and extracted with $CHCl_3$/MeOH (v/v=10:1). The organic layer was dried over anhydrous $MgSO_4$ and then filtered and concentrated under reduced pressure to give crude product, which was purified via silica gel column chromatography (CHCl$_3$/MeOH (v/v)=20:1) to give pure yellow solid (130 mg, 33.1% yield).

$^1$H-NMR (CDCl$_3$) δ: 0.98 (t, J=7.2 Hz, 3H, CH$_2$CH$_2$CH$_3$), 1.71 (q, J=7.2 Hz, 2H, CH$_2$CH$_2$CH$_3$), 2.90 (s, 3H, ArCH$_3$), 2.90-3.01 (m, 2H, CH$_2$CH$_2$CH$_3$), 3.04-3.14 (m, 1H, NCH$_2$CH$_2$), 3.28-3.36 (m, 1H, NCH$_2$CH$_2$), 4.26-4.28 (m, 1H, NCH$_2$CH$_2$), 4.94-5.01 (m, 1H, NCH$_2$CH$_2$), 6.05 (br s, 2H, OCH$_2$O), 6.16 (s, 1H, OCH$_2$O), 6.27 (s, 1H, OCH$_2$O), 6.82 (s, 1H, ArH), 7.03 (s, 1H, ArH), 7.15 (s, 1H, C=CH$_2$), 7.32 (s, 1H, C=CH$_2$), 7.66 (d, J=8.7 Hz, 1H, ArH), 7.80 (d, J=8.7 Hz, 1H, ArH). MS (m/z): 430.2 [M-Cl]$^+$.

Preparation of Compound 14

To a stirred solution of coptisine (190 mg, 0.53 mmol) in 5 N NaOH (1 ml), 2-hexanone (0.5 mL, 4.04 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (4 mL) followed by addition of HOAc (1 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (106 mg, 41.4% yield).

$^1$H-NMR (DMSO-d$_6$) δ: 0.91 (m, 3H, CH$_2$CH$_2$CH$_2$CH$_3$), 1.36 (m, 2H, CH$_2$CH$_2$CH$_2$CH$_3$), 1.58 (m, 2H, CH$_2$CH$_2$CH$_2$CH$_3$), 2.91 (s, 3H, ArCH$_3$), 2.91-3.05 (m, 2H, CH$_2$CH$_2$CH$_2$CH$_3$), 3.05-3.16 (m, 2H, NCH$_2$CH$_2$), 4.22 (s, 2H, NCH$_2$CH$_2$), 6.16 (s, 2H, OCH$_2$O), 6.25 (s, 1H, OCH$_2$O), 6.36 (s, 1H, OCH$_2$O), 6.78 (s, 1H, C=CH$_2$), 7.14 (s, 1H, ArH), 7.19 (s, 1H, C=CH$_2$), 7.39 (s, 1H, ArH), 8.03 (s, 1H, ArH). MS (m/z): 444.2 (M-Cl)$^+$.

Preparation of Compound 15

To a stirred solution of coptisine (300 mg, 0.84 mmol) in 5 N NaOH (1.5 ml), 2-heptanone (1 mL, 7.18 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (5 mL) followed by addition of HOAc (1 mL) and formaldehyde (1.5 mL, 15.06 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (97 mg, 23.3% yield).

$^1$H-NMR (DMSO-d$_6$) δ: 0.91 (br s, 3H, CH$_2$CH$_2$(CH$_2$)$_2$CH$_3$), 1.33-1.35 (m, 4H, CH$_2$CH$_2$(CH$_2$)$_2$CH$_3$), 1.58-1.61 (m, 2H, CH$_2$CH$_2$(CH$_2$)$_2$CH$_3$), 2.93 (s, 3H, ArCH$_3$), 2.93-3.14 (m, 4H, CH$_2$CH$_2$(CH$_2$)$_2$CH$_3$, NCH$_2$CH$_2$), 4.45 (br s, 2H, NCH$_2$CH$_2$), 6.18 (s, 2H, OCH$_2$O), 6.29 (s, 1H, OCH$_2$O), 6.40 (s, 1H, OCH$_2$O), 6.79 (s, 1H, C=CH$_2$), 7.16 (s, 1H, ArH), 7.19 (s, 1H, C=CH$_2$), 7.42 (s, 1H, ArH), 8.05 (s, 2H, ArH). MS (m/z): 458.2 (M-Cl)$^+$.

Preparation of Compound 16

To a stirred solution of coptisine (200 mg, 0.56 mmol) in 5 N NaOH (1 ml), 2-octanone (1 mL, 6.26 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (4 mL) followed by addition of HOAc (0.5 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid. (65 mg, 22.8% yield)

$^1$H-NMR (DMSO-d$_6$) δ: 0.88 (br s, 3H, CH$_2$CH$_2$(CH$_2$)$_3$CH$_3$), 1.31 (br s, 6H, CH$_2$CH$_2$(CH$_2$)$_3$CH$_3$), 1.58-1.60 (m, 2H, CH$_2$CH$_2$(CH$_2$)$_3$CH$_3$), 2.73-3.15 (m, 4H, CH$_2$CH$_2$(CH$_2$)$_3$CH$_3$, NCH$_2$CH$_2$), 2.93 (s, 3H, ArCH$_3$), 4.45 (br s, 2H, NCH$_2$CH$_2$), 6.18 (s, 2H, OCH$_2$O), 6.29 (s, 1H, OCH$_2$O), 6.40 (s, 1H, OCH$_2$O), 6.78 (s, 1H, C=CH$_2$), 7.16 (s, 1H, ArH), 7.19 (s, 1H, C=CH$_2$), 7.42 (s, 1H, ArH), 8.05 (s, 2H, ArH).

Preparation of Compound 17

To a stirred solution of coptisine (100 mg, 0.28 mmol) in 5 N NaOH (1 ml), 2-nonanone (0.5 mL, 2.91 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (3 mL) followed by addition of HOAc (0.5 mL) and formaldehyde (0.6 mL, 6.02 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (30 mg, 20.4% yield).

$^1$H-NMR (DMSO-d$_6$) δ: 0.87 (br s, 3H, CH$_2$CH$_2$(CH$_2$)$_4$CH$_3$), 1.28-1.31 (m, 8H, CH$_2$CH$_2$(CH$_2$)$_4$CH$_3$), 1.58-1.61 (m, 2H, CH$_2$CH$_2$(CH$_2$)$_4$C$_3$), 2.83-3.15 (m, 4H, CH$_2$CH$_2$(CH$_2$)$_4$CH$_3$, NCH$_2$CH$_2$), 2.93 (s, 3H, ArCH$_3$), 4.45 (br s, 2H, NCH$_2$CH$_2$), 6.18 (s, 2H, OCH$_2$O), 6.29 (s, 1H, OCH$_2$O), 6.40 (s, 1H, OCH$_2$O), 6.78 (s, 1H, C=CH$_2$), 7.16 (s, 1H, ArH), 7.19 (s, 1H, C=CH$_2$), 7.42 (s, 1H, ArH), 8.05 (s, 2H, ArH).

Preparation of Compound 18

To a stirred solution of coptisine (200 mg, 0.56 mmol) in 5 N NaOH (1 ml), 2-decanone (1 mL, 5.28 mmol) was added dropwise. The reaction mixture was stirred at 60° C. for 3 h. The reaction mixture was extracted with CHCl₃/MeOH (v/v=10:1). The organic layer was washed to neutral with water, and dried over anhydrous MgSO₄, and filtered, and then concentrated under reduced pressure to give intermediate product. The intermediate product was dissolved in anhydrous tetrahydrofuran (4 mL) followed by addition of HOAc (0.5 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl₃/MeOH (v/v=10:1). The organic layer was dried over anhydrous MgSO₄ and then filtered and concentrated under reduced pressure to give crude product, which was purified via silica gel column chromatography (CHCl₃/MeOH (v/v)=20:1) to give pure yellow solid (59 mg, 19.6% yield).

¹H-NMR (DMSO-$d_6$) δ: 0.88 (t, J=9.0 Hz, 3H, CH₂CH₂(CH₂)₅C$\underline{H}$₃), 1.27 (br s, 10H, CH₂CH₂(C$\underline{H}$₂)₅CH₃), 1.58-1.61 (m, 2H, CH₂C$\underline{H}$₂(CH₂)₅CH₃), 2.93 (s, 3H, ArCH₃), 2.93-3.15 (m, 4H, C$\underline{H}$₂CH₂(CH₂)₅CH₃, NCH₂C$\underline{H}$₂), 4.45 (br s, 2H, NC$\underline{H}$₂CH₂), 6.18 (br s, 2H, OCH₂O), 6.29 (s, 1H, OCH₂O), 6.40 (s, 1H, OCH₂O), 6.79 (s, 1H, C=CH₂), 7.16 (s, 1H, ArH), 7.19 (s, 1H, C=CH₂), 7.42 (s, 1H, ArH), 8.05 (s, 2H, ArH).

Preparation of Compound 19

To a stirred solution of coptisine (200 mg, 0.56 mmol) in 5 N NaOH (1 ml), 2-undecanone (1 mL, 4.87 mmol) was added dropwise. The reaction mixture was stirred at 60° C. for 3 h. The reaction mixture was extracted with CHCl₃/MeOH (v/v=10:1). The organic layer was washed to neutral with water, and dried over anhydrous MgSO₄, and filtered, and then concentrated under reduced pressure to give intermediate product. The intermediate product was dissolved in anhydrous tetrahydrofuran (4 mL) followed by addition of HOAc (0.5 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl₃/MeOH (v/v=10:1). The organic layer was dried over anhydrous MgSO₄ and then filtered and concentrated under reduced pressure to give crude product, which was purified via silica gel column chromatography (CHCl₃/MeOH (v/v)=20:1) to give pure yellow solid (55 mg, 17.8% yield).

¹H-NMR (DMSO-$d_6$) δ: 0.86 (t, J=6.6 Hz, 3H, CH₂CH₂(CH₂)₆C$\underline{H}$₃), 1.26-1.31 (m, 12H, CH₂CH₂(C$\underline{H}$₂)₆CH₃), 1.58-1.60 (m, 2H, CH₂C$\underline{H}$₂(CH₂)₆CH₃), 2.93 (s, 3H, ArCH₃), 2.93-3.14 (m, 4H, C$\underline{H}$₂CH₂(CH₂)₆CH₃, NCH₂C$\underline{H}$₂), 4.45 (br s, 2H, NC$\underline{H}$₂CH₂), 6.18 (br s, 2H, OCH₂O), 6.29 (s, 1H, OCH₂O), 6.40 (s, 1H, OCH₂O), 6.78 (s, 1H, C=CH₂), 7.16 (s, 1H, ArH), 7.18 (s, 1H, C=CH₂), 7.42 (s, 1H, ArH), 8.05 (s, 2H, ArH).

Preparation of Compound 20

To a stirred solution of coptisine (230 mg, 0.65 mmol) in 5 N NaOH (1 ml), methoxyacetophenone (780 mg, 5.19 mmol) was added slowly. The reaction mixture was stirred at 60° C. for 3 h. The reaction mixture was extracted with CHCl₃/MeOH (v/v=10:1). The organic layer was washed to neutral with water, and dried over anhydrous MgSO₄, and filtered, and then concentrated under reduced pressure to give intermediate product. The intermediate product was dissolved in anhydrous tetrahydrofuran (4 mL) followed by addition of HOAc (0.5 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl₃/MeOH (v/v=10:1). The organic layer was dried over anhydrous MgSO₄ and then filtered and concentrated under reduced pressure to give crude product, which was purified via silica gel column chromatography (CHCl₃/MeOH (v/v)=20:1) to give pure yellow solid (140 mg, 41.0% yield).

¹H-NMR (DMSO-$d_6$) δ: 2.94 (s, 3H, OCH₃), 2.94-3.13 (m, 2H, NCH₂C$\underline{H}$₂), 3.89 (s, 3H, ArCH₃), 4.54 (br s, 2H, NC$\underline{H}$₂CH₂), 6.17 (s, 2H, OCH₂O), 6.19 (s, 1H, OCH₂O), 6.43 (s, 1H, OCH₂O), 6.83 (s, 1H, C=CH₂), 6.97 (s, 1H, C=CH₂), 7.15 (d, J=9.0 Hz, 2H, ArH), 7.16 (s, 1H, ArH), 7.42 (s, 1H, ArH), 7.97 (d, J=8.7 Hz, 2H, ArH), 8.06 (m, 2H, ArH). MS (m/z): 494.2 (M-Cl)⁺.

Preparation of Compound 21

To a stirred solution of coptisine (100 mg, 0.28 mmol) in 5 N NaOH (1 ml), 1-acetonaphthone (0.5 mL, 3.28 mmol) was added dropwise. The reaction mixture was stirred at 60° C. for 3 h. The reaction mixture was extracted with CHCl₃/MeOH (v/v=10:1). The organic layer was washed to neutral with water, and dried over anhydrous MgSO₄, and filtered, and then concentrated under reduced pressure to give intermediate product. The intermediate product was dissolved in anhydrous tetrahydrofuran (3 mL) followed by addition of HOAc (0.5 mL) and formaldehyde (0.6 mL, 6.02 mmol) dropwise. The reaction mixture was kept refluxing for 3 h. After the reaction completed, the reaction mixture was concentrated and added with 2 N HCl (2 mL), then stirred at room temperature for 1 h and extracted with CHCl₃/MeOH (v/v=10:1). The organic layer was dried over anhydrous MgSO₄ and then filtered and concentrated under reduced pressure to give crude product, which was purified via silica gel column chromatography (CHCl₃/MeOH (v/v)=20:1) to give pure yellow solid (34 mg, 22.1% yield).

¹H-NMR (DMSO-$d_6$) δ: 2.98 (s, 3H, ArCH₃), 3.10-3.20 (m, 2H, NCH₂C$\underline{H}$₂), 4.57-4.78 (m, 2H, NC$\underline{H}$₂CH₂), 6.18 (s, 2H, OCH₂O), 6.44 (d, J=9.9 Hz, 2H, OCH₂O), 6.82 (s, 1H, C=CH₂), 7.08 (s, 1H, C=CH₂), 7.20 (s, 1H, ArH), 7.460 (s, 1H, ArH), 7.64-7.76 (m, 2H, ArH), 8.04-8.14 (m, 4H, ArH), 8.24 (d, J=8.4 Hz, 1H, ArH).

Preparation of Compound 22

To a stirred solution of coptisine (250 mg, 0.70 mmol) in 5 N NaOH (1 ml), 6-acetyl-1,4-benzodioxane (1 mL, 6.67 mmol) was added slowly. The reaction mixture was stirred at 60° C. for 3 h. The reaction mixture was extracted with CHCl₃/MeOH (v/v=10:1). The organic layer was washed to neutral with water, and dried over anhydrous MgSO₄, and filtered, and then concentrated under reduced pressure to give intermediate product. The intermediate product was dissolved in anhydrous tetrahydrofuran (5 mL) followed by addition of HOAc (0.5 mL) and formaldehyde (1.5 mL, 15.06 mmol) dropwise. The reaction mixture was kept refluxing for 3 h. After the reaction completed, the reaction mixture was concentrated and added with 2 N HCl (2 mL), then stirred at room temperature for 1 h and extracted with CHCl₃/MeOH (v/v=10:1). The organic layer was dried over anhydrous MgSO₄ and then filtered and concentrated under reduced pressure to give crude product, which was purified via silica gel column chromatography (CHCl₃/MeOH (v/v)=20:1) to give pure yellow solid (110 mg, 28.1% yield).

$^1$H-NMR (DMSO-d$_6$) δ: 2.95 (s, 3H, ArCH$_3$), 2.99-3.14 (m, 2H, NCH$_2$CH$_2$), 4.37 (br d, J=9.0 Hz, 4H, OCH$_2$CH$_2$O), 4.54 (br s, 2H, NCH$_2$CH$_2$), 6.19 (s, 2H, OCH$_2$O), 6.24 (s, 1H, OCH$_2$O), 6.44 (s, 1H, OCH$_2$O), 6.86 (s, 1H, C=CH$_2$), 6.99 (s, 1H, C=CH$_2$), 7.10 (d, J=8.4 Hz, 1H, ArH), 7.17 (s, 1H, ArH), 7.44 (s, 1H, ArH), 7.45 (d, J=2.1 Hz, 2H, ArH), 7.54 (dd, J$_1$=8.4 Hz, J$_2$=2.1 Hz, 1H, ArH), 8.07 (s, 2H, ArH).

Preparation of Compound 23

To a stirred solution of coptisine (200 mg, 0.56 mmol) in 5 N NaOH (1 ml), 4-isobutylacetophenone (1 mL, 5.40 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (4 mL) followed by addition of HOAc (0.5 mL) and formaldehyde (1 mL, 10.04 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (117 mg, 37.4% yield).
$^1$H-NMR (DMSO-d$_6$) δ: 0.92 (d, J=6.6 Hz, 6H, CH$_2$CH(CH$_3$)$_2$), 1.89-1.96 (m, 1H, CH$_2$CH(CH$_3$)$_2$), 2.60 (d, J=6.9 Hz, 2H, CH$_2$CH(CH$_3$)$_2$), 2.96 (s, 3H, ArCH$_3$), 2.99-3.14 (m, 2H, NCH$_2$CH$_2$), 4.56 (br s, 2H, NCH$_2$CH$_2$), 6.19 (br s, 2H, OCH$_2$O), 6.25 (s, 1H, OCH$_2$O), 6.45 (s, 1H, OCH$_2$O), 6.87 (s, 1H, C=CH$_2$), 7.03 (s, 1H, C=CH$_2$), 7.18 (s, 1H, ArH), 7.43 (d, J=7.5 Hz, 2H, ArH), 7.44 (s, 1H, ArH), 7.89 (d, J=7.5 Hz, 2H, ArH), 8.05 (s, 2H, ArH).

Preparation of Compound 24

To a stirred solution of coptisine (250 mg, 0.70 mmol) in 5 N NaOH (1 ml), acetophenone (0.8 mL, 6.85 mmol) was added slowly. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (5 mL) followed by addition of HOAc (0.5 mL) and formaldehyde (1.5 mL, 15.06 mmol) dropwise. The reaction mixture was kept refluxing for 3 h. After the reaction completed, the reaction mixture was concentrated and added with 2 N HCl (2 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure deep yellow solid (120 mg, 34.3% yield).
$^1$H-NMR (DMSO-d$_6$) δ (ppm): 2.96 (s, 3H, ArCH$_3$), 2.96-3.15 (m, 2H, NCH$_2$CH$_2$), 4.58 (br s, 2H, NCH$_2$CH$_2$), 6.19 (s, 2H, OCH$_2$O), 6.26 (s, 1H, OCH$_2$O), 6.46 (s, 1H, OCH$_2$O), 6.88 (s, 1H, C=CH$_2$), 7.07 (s, 1H, C=CH$_2$), 7.18 (s, 1H, ArH), 7.45 (s, 1H, ArH), 7.62-7.67 (m, 2H, ArH), 7.76 (t, J=7.2 Hz, 1H, ArH), 7.96 (d, J=7.8 Hz, 2H, ArH), 8.08 (m, 2H, ArH).

Preparation of Compound 25

To a stirred solution of coptisine (100 mg, 0.28 mmol) in 5 N NaOH (0.8 ml), pinacotone (0.2 mL, 1.60 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (4 mL) followed by addition of HOAc (0.3 mL) and formaldehyde (0.3 mL, 3.01 mmol) dropwise. The reaction mixture was kept refluxing for 1 h. After the reaction completed, the reaction mixture was concentrated and added with 2 N HCl (1.5 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (30 mg, 22.2% yield).
$^1$H-NMR (CDCl$_3$) δ (ppm): 1.48 (s, 9H, 3CH$_3$), 2.92 (s, 3H, ArCH$_3$), 2.96-2.99 (m, 1H, NCH$_2$CH$_2$), 3.42-3.49 (m, 1H, NCH$_2$CH$_2$), 4.09-4.15 (m, 1H, NCH$_2$CH$_2$), 5.08-5.14 (m, 1H, NCH$_2$CH$_2$), 6.07-6.09 (m, 2H, OCH$_2$O), 6.20 (s, 1H, OCH$_2$O), 6.29 (s, 1H, OCH$_2$O), 6.84 (s, 1H, ArH), 7.06 (s, 1H, ArH), 7.23 (s, 1H, C=CH$_2$), 7.64 (s, 1H, C=CH$_2$), 7.67 (d, J=9.0 Hz, 1H, ArH), 7.80 (d, J=9.0 Hz, 1H, ArH). MS (m/z): 444.2 (M-Cl)$^+$.

Preparation of Compound 26

To a stirred solution of coptisine (300 mg, 0.84 mmol) in 5 N NaOH (1.5 ml), 3-methyl-2-butanone (0.5 mL, 4.70 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (5 mL) followed by addition of HOAc (1.2 mL) and formaldehyde (1 mL, 10.04 mmol) dropwise. The reaction mixture was kept refluxing for 1 h. After the reaction completed, the reaction mixture was concentrated and added with 2 N HCl (2.5 mL), then stirred at room temperature for 1 h and extracted with CHCl$_3$/MeOH (v/v=10:1). The organic layer was dried over anhydrous MgSO$_4$ and then filtered and concentrated under reduced pressure to give crude product, which was purified via silica gel column chromatography (CHCl$_3$/MeOH (v/v)=20:1) to give pure yellow solid (140 mg, 35.6% yield).
$^1$H-NMR (DMSO-d$_6$) δ (ppm): 1.16-1.20 (m, 6H, 2CH$_3$), 2.92 (s, 3H, ArCH$_3$), 2.87-3.10 (m, 2H, NCH$_2$CH$_2$), 3.67-3.76 (m, 1H, COCH), 4.27-4.50 (m, 2H, NCH$_2$CH$_2$), 6.17 (s, 2H, OCH$_2$O), 6.31 (s, 1H, OCH$_2$O), 6.39 (s, 1H, OCH$_2$O), 6.85 (s, 1H, C=CH$_2$), 7.15 (s, 1H, ArH), 7.28 (s, 1H, C=CH$_2$), 7.41 (s, 1H, ArH), 8.04 (s, 2H, ArH). MS (m/z): 430.2 (M-Cl)$^+$.

Preparation of Compound 27

To a stirred solution of coptisine (300 mg, 0.84 mmol) in 5N NaOH (1.5 ml), methyl cyclopropyl ketone (0.4 mL, 4.27 mmol) was added dropwise. The reaction mixture was stirred at 60° C. for 3 h. The reaction mixture was extracted with CHCl$_3$/MeOH (v/v=10:1). The organic layer was washed to neutral with water, and dried over anhydrous MgSO$_4$, and filtered, and then concentrated under reduced pressure to give intermediate product. The intermediate product was dissolved in anhydrous tetrahydrofuran (5 mL) followed by addition of HOAc (1.2 mL) and formaldehyde (1 mL, 10.04 mmol) dropwise. The reaction mixture was kept refluxing for 1 h. After the reaction completed, the reaction mixture was concentrated and added with 2 N HCl (2.5 mL), then stirred at room temperature for 1 h and extracted with $CHCl_3$/MeOH (v/v=10:1). The organic layer was dried over anhydrous $MgSO_4$ and then filtered and concentrated under reduced pressure to give crude product, which was purified via silica gel column chromatography ($CHCl_3$/MeOH (v/v)=20:1) to give pure yellow solid (204 mg, 52.1% yield).

$^1$H-NMR (DMSO-$d_6$) δ (ppm): 1.03-1.13 (m, 4H, 2$CH_2$), 2.93 (s, 3H, Ar$CH_3$), 2.93-3.12 (m, 3H, N$CH_2$C$\underline{H}_2$, COCH), 4.42-4.46 (m, 2H, NC$\underline{H}_2$C$H_2$), 6.18 (s, 2H, O$CH_2$O), 6.33 (s, 1H, O$CH_2$O), 6.44 (s, 1H, O$CH_2$O), 6.85 (s, 1H, C=$CH_2$), 7.16 (s, 1H, ArH), 7.39 (s, 1H, C=$CH_2$), 7.41 (s, 1H, ArH), 8.05 (s, 2H, ArH). MS (m/z): 428.2 (M-Cl)$^+$.

Preparation of Compound 28

To a stirred solution of coptisine (300 mg, 0.84 mmol) in 5N NaOH (1.5 ml), methyl cyclohexyl ketone (0.6 mL, 4.37 mmol) was added dropwise. The reaction mixture was stirred at 60° C. for 3 h. The reaction mixture was extracted with $CHCl_3$/MeOH (v/v=10:1). The organic layer was washed to neutral with water, and dried over anhydrous $MgSO_4$, and filtered, and then concentrated under reduced pressure to give the intermediate product. The intermediate product was dissolved in anhydrous tetrahydrofuran (5 mL) followed by addition of HOAc (1.2 mL) and formaldehyde (1 mL, 10.04 mmol) dropwise. The reaction mixture was kept refluxing for 1 h. After the reaction finished, the reaction mixture was concentrated and added with 2 N HCl (2.5 mL), then stirred at room temperature for 1 h and extracted with $CHCl_3$/MeOH (v/v=10:1). The organic layer was dried over anhydrous $MgSO_4$ and then filtered and concentrated under reduced pressure to give crude product, which was purified via silica gel column chromatography ($CHCl_3$/MeOH (v/v)=20:1) to give pure yellow solid (105 mg, 24.7% yield).

$^1$H-NMR (DMSO-$d_6$) δ (ppm): 1.14-1.95 (m, 10H, 5$CH_2$), 2.85-3.14 (m, 2H, N$CH_2$C$\underline{H}_2$), 2.91 (s, 3H, Ar$CH_3$), 3.44-3.51 (m, 1H, COCH), 4.23-4.49 (m, 2H, NC$\underline{H}_2$C$H_2$), 6.16 (s, 2H, O$CH_2$O), 6.29 (s, 1H, O$CH_2$O), 6.38 (s, 1H, O$CH_2$O), 6.82 (s, 1H, C=$CH_2$), 7.14 (s, 1H, ArH), 7.28 (s, 1H, C=$CH_2$), 7.40 (s, 1H, ArH), 8.03 (s, 2H, ArH). MS (m/z): 470.2 (M-Cl)$^+$.

Preparation of Compound 29

To a stirred solution of 13-methylcoptisine (41 mg, 0.11 mmol) and $K_2CO_3$ (45 mg, 0.33 mmol) in methanol (4 mL), 5% NaOH solution (0.5 mL) containing $NaBH_4$ (6 mg, 0.16 mmol) was added dropwise. The reaction mixture was stirred at room temperature for 2 h until the reaction completed and the precipitated product was filtered, washed to neutral with water and then dried to give yellow solid (28 mg, 75.7% yield).

$^1$H-NMR (DMSO-$d_6$) δ (ppm): 2.15 (s, 3H, Ar$CH_3$), 2.68 (br s, 2H, N$CH_2$C$H_2$), 3.03 (br s, 2H, N$CH_2$C$H_2$), 4.14 (s, 2H, N$CH_2$Ar), 6.00 (s, 1H, O$CH_2$O), 6.03 (s, 2H, O$CH_2$O), 6.64 (d, J=8.1 Hz, 1H, ArH), 6.77 (d, J=8.1 Hz, 1H, ArH), 6.84 (s, 1H, ArH), 7.03 (s, 1H, ArH).

Pharmacological Experiment 1

Example of Bioresearch on Compounds for Anti-UC

1. Cytotoxicity Assay of Compounds (1) Method: Intestinal epithelial cell IEC-6 at high confluence (>90%) were digested with 0.25% trypsin/0.1% EDTA and then seeded in a 96-well plate at a density of $2\times10^3$/well. The next day the medium was discarded and cultivated with testcompounds at $1\times10^{-5}$ mol/L. The cytotoxicity was measured by MTT assay (n=5) at 0 h, 24 h, and 72 h after co-culture of IEC-6 cells and test compounds.

(2) Results: During the test, $1\times10^{-5}$ mol/L test compounds according to the present invention did not show significant cytotoxicity on IEC-6 cell. There was no significant difference statistically (FIG. 1).

(3) Conclusion: A series of protoberberine alkaloid derivatives or its physiologically acceptable salts according to the present invention are suitable for screening downstream experiment with IEC-6 cell model.

The cytotoxicity test results on IEC-6 cell model of protoberberine alkaloid derivatives or their physiologically acceptable salts according to the present invention at 1 uM are shown in FIG. 1. It is shown that, in addition to the compounds 16-19 and 21, the other test compounds have no significant cytotoxicity when incubated with IEC-6 cells for 24 h at this concentration. The result after 3 days is the same as that after 24 h (data not shown here) and does not show significant cytotoxicity.

2. Transcriptional Activation Effect on pGL3-pxbp1 of 24 Test Compounds with No Obvious Cytoxity on IEC-6 Cell (1) Method: IEC-6 cells in the period of vigorous growth were seed in 48 well plate at a density of $5\times10^4$ to disperse the cells uniform and then it was placed in a humidifying cell incubator filled with 5% $CO_2$ at 37° C. to incubate. Plasmid transfection (0.6 μg/well) was carried out when the cells confluencing up to 70%-80%. After 4 h, each compound of $1\times10^{-5}$ mol/L was added into these wells (n=3), respectively, and incubated for another 36 h-48 h together with existing transfected cells. Luciferase activity detection on test samples was proceeded using dual luciferase report gene detection kit (Promega, USA).

(2) Results: According to the statistical analysis, 24 test compounds were found to show transcriptional activation effect on the xbp1 upstream promoter as compared with controls (with non-transfected plasmid cells as control group 1, and transfected cells by pGL-xbp1 without compound as control group 2).

(3) Conclusion: The protoberberine alkaloid derivatives or their physiologically acceptable salts according to the present invention show transcription activation effect on the expression of xbp1 gene.

Figure 2:
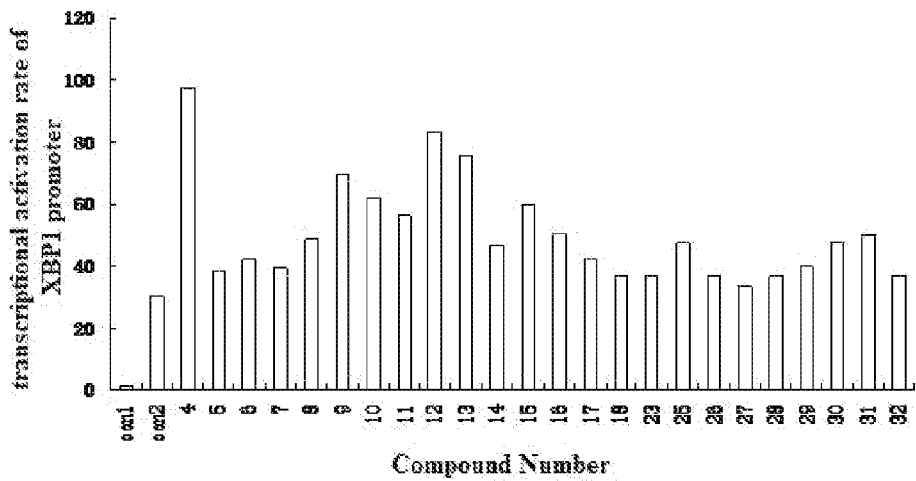
FIG. 2 shows the results of activating effect on xbp1 upstream promoter of different compounds of the present invention.
Figure 3:
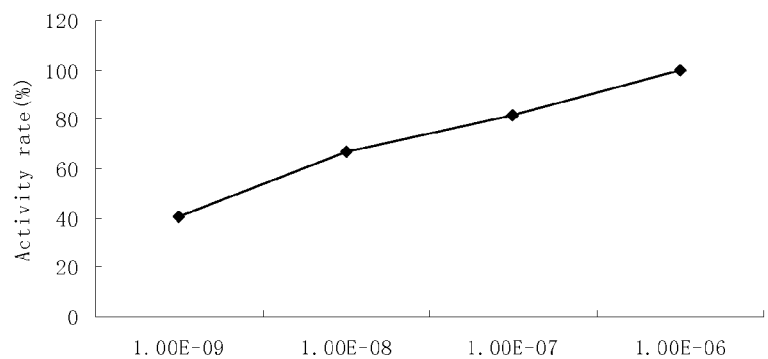
FIG. 3 shows that the $EC_{50}$ value of compound 1 is $2.29 \times 10^{-9}$ (mol/L).
Figure 3:
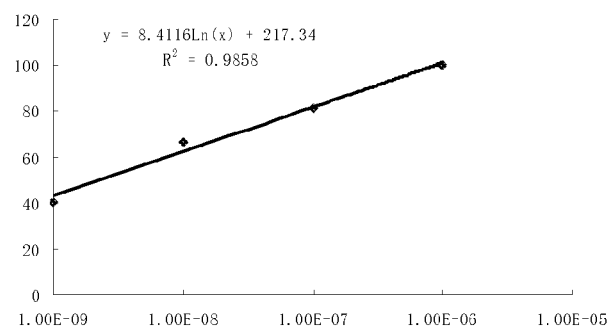
Figure 4:
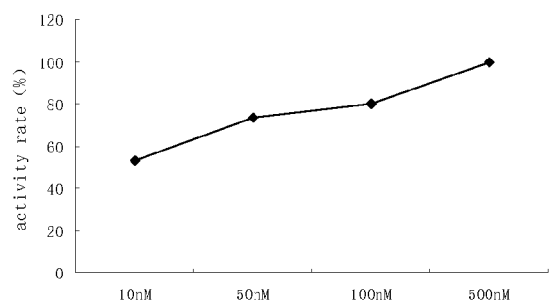
FIG. 4 shows that the $EC_{50}$ value of compound 2 is $7.06 \times 10^{-9}$ (mol/L).
Figure 4:
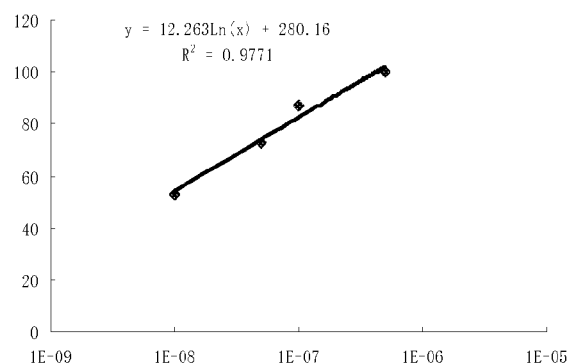
Figure 5:
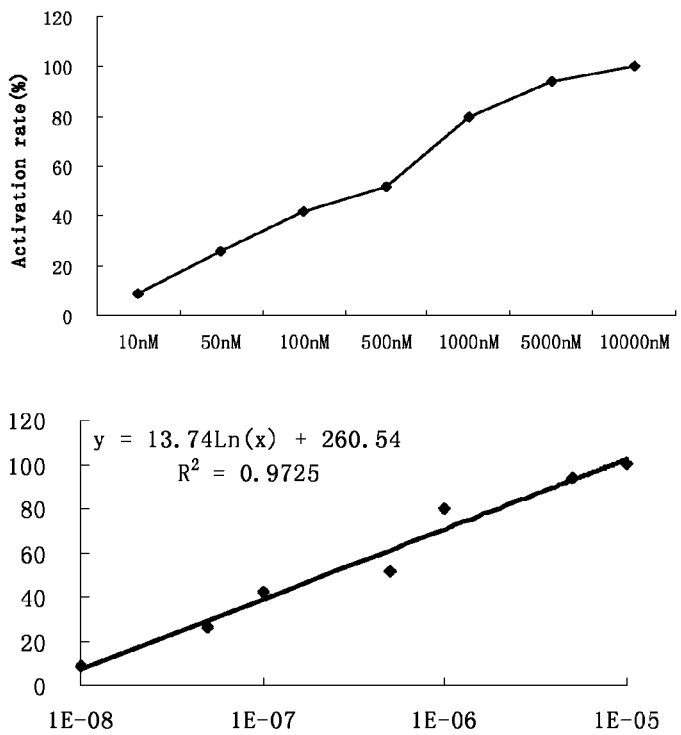
FIG. 5 shows that the $EC_{50}$ value of compound 7 is $2.21 \times 10^{-7}$ (mol/L).
Figure 6:
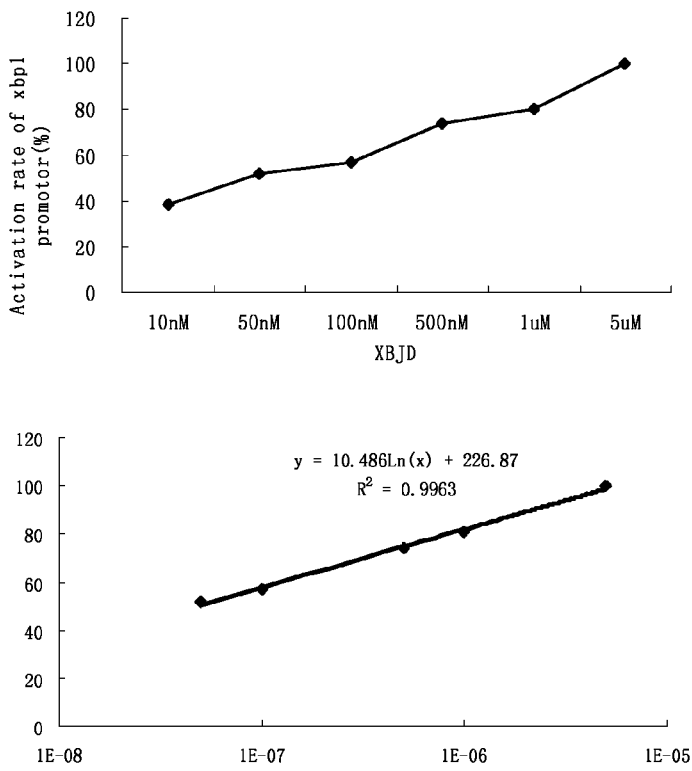
FIG. 6 shows that the $EC_{50}$ value of compound 10 is $4.73 \times 10^{-8}$ (mol/L).

The experimental results are shown in FIG. 2.

Different test compounds have certain transcriptional activation effect on xbp1 gene promoter. In FIG. 2, con 1 is used as background and con 2 is pGL3 empty vector control. The results show that these new compounds can activate the transcription of xbp1 molecule to varying degrees, and thus have certain transcriptional activation effect.

3. Determination of $EC_{50}$ Values of Compounds 1, 2, 7, and 10

(1) Method: IEC-6 cells in the period of logarithmic phase were seed in 48 well plate at a density of $5\times10^4$ to disperse the cells uniform and then it was placed in a humidifying cell incubator filled with 5% $CO_2$ at 37° C. to incubate. Plasmid transfection (0.6 μg/well) was carried out when the cells confluencing up to 70%-80%. After 4 h, different concentrations of compounds 1, 2, 7, and 10 were added (n=3), respectively, and incubated for another 36 h-48 h together with existing transfected cells. Luciferase activity detection on test samples was proceeded using dual luciferase report gene detection kit (Promega, USA).

(2) Results: The experimental results are shown in FIGS. 3-6.

4. In vivo Test Results of Compound 7

(1) Method: In vivo test was carried out according to the literature: Y. Yoshioka, H. Akiyama, M. Nakano, T. Shoji, T. Kanda, Y. Ohtake, T. Takita, R. Matsuda, T. Maitani. Orally administered apple procyanidins protect against experimental inflammatory bowel disease in mice, international immunopharmacology, 2008, 1802-1807.

(2) Results and conclusions: Compound 7 has preliminary therapeutic effect on acute UC SD rats induced by acetic acid in vivo.

Figure 7:
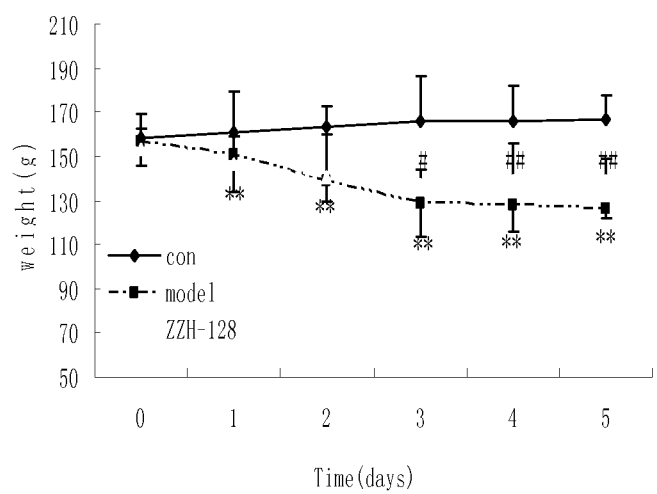
FIG. 7 shows the effect of compound 7 on the weight of rats suffering from UC.

① Compound 7 can reduce the weight loss in SD rats suffering from UC induced by acetic acid (FIG. 7).

As shown in FIG. 7, compared to the normal control group (blue curve), body weight of the model group (red curve) is decreased significantly (**P<0.01); compound 7 group (300 mg/kg) (green curve) can reduce the weight loss of the animals when compared to the model group (red curve) (#p<0.05, ##p<0.01). These test results show that compound 7 of 300 mg/kg can reduce the weight loss of SD rats suffering from UC to a certain extent. Comparing with the case before administration, the body weight change value of each group is: for the normal control group it is increased by 5.6%; for the model group it is decreased by 19.2%; and for compound 7 group it is decreased by 10%.

Figure 8:
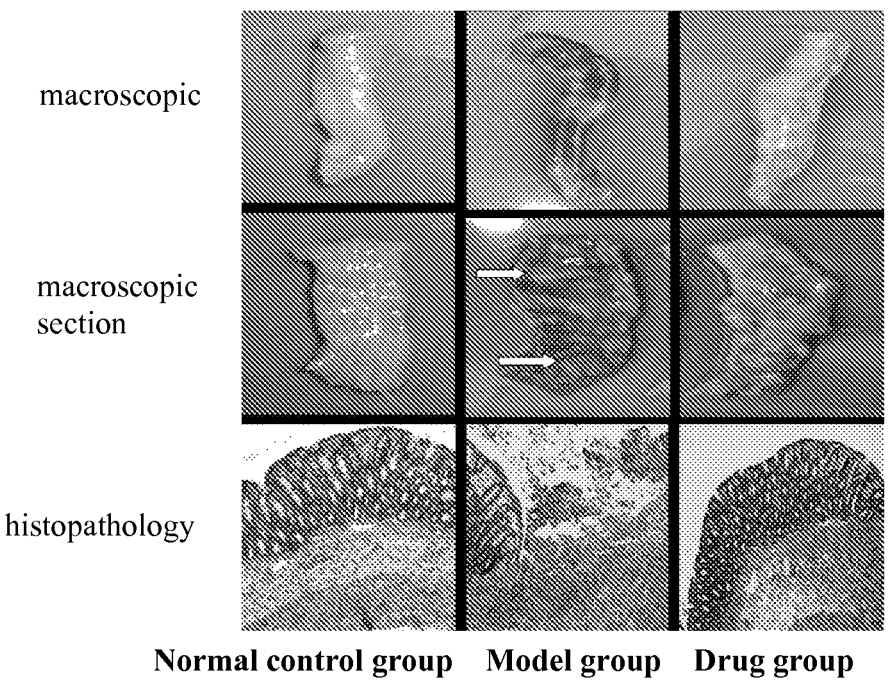
FIG. 8 shows the effect of compound 7 on the pathological change of colon tissue of rats suffering from UC.

Compound 7 (300 mg/kg) can improve the inflammatory damage on SD rats suffering from UC induced by acetic acid (FIG. 8).

As shown in FIG. 8, for the normal control group it is observed that there is visible smooth intestinal wall and proper film tension, with mucosa without edema, hemorrhage, and obvious ulcer and that the histopathological examination shows that the structure in each layer of colon is normal without inflammatory change. While for the model group, severe swell can be seen in intestinal wall of colon tissue with obvious hemorrhage and exudation, and about 1 cm diameter ulcer is also seen in mucous layer (white arrow), the pathological section shows typical inflammatory characters with structure damage in each layer of colonic tissue. For drug groups, both the macroscopic and the histopathological results show that compound 7 has good therapeutic effect on UC, with inflammatory edema and hemorrhage being significantly reduced, and the intestinal epithelial cells even returning to normal alignment and regular polarity.

② Effect of compound 7 on disease activity index (DAI) and macroscopic score of colon tissue in SD rats with acetic acid-induced UC (see Table 1).

Disease activity index (DAI) is evaluated by weight loss, shape of stool, hematochezia, and other indicators; macroscopic score of colon tissue is evaluated by intestinal mucosal hyperemia, edema of intestinal wall, ulcer size, and other indicators. The lower the DAI and macroscopic score is, the more close to the normal physiological state. In Table 1: **p<0.01 when compared with the normal control group; ##p<0.01 when compared with the model group.

TABLE 1

Effect of different groups on DAI and macroscopic score of colon tissue in SD rats with acetic acid-induced UC

| Groups | n (start/end) | DAI | macroscopic score |
|---|---|---|---|
| Normal control group | 6/6 | 0.00 ± 0.00 | 0.12 ± 0.00 |
| Model group (acetic acid-induced) | 6/6 | 3.15 ± 0.45** | 0.12 ± 0.00 |
| Compound 7 group (300 mg/kg) | 6/6 | 1.15 ± 0.22## | 2.05 ± 0.45## |

④ Compound 7 can efficiently reduce the weight loss in C57/blc mice with DSS-induced UC in a good dose-dependent manner (see Table 2).

In Table 2, **p<0.01 when compared with the normal control group; ##p<0.01 when compared with the model group. The inhibitory effect of compound 7 of high dose (HD) group on the weight loss of experimental animal is even more prominent than that of the clinical conventional drug SASP for treating UC.

TABLE 2

The therapeutic effect of compound 7 on C57/blc mice with DSS-induced acute UC in vivo

| Groups | n (start/end) | Body weight (g) x ± SD | | Change of body weight (%) |
|---|---|---|---|---|
| | | start | end | |
| Normal control group | 10/10 | 23.02 ± 1.2 | 24.43 ± 0.8 | ↑ 6.14 |
| Model group (DSS-induced) | 10/10 | 23.83 ± 1.3 | 17.51 ± 2.1 | ↓ 26.52** |
| SASP group (300 mg/kg) | 10/10 | 23.83 ± 2.3 | 20.09 ± 0.9 | ↓ 15.69## |
| Compound 7 HD group (500 mg/kg) | 10/10 | 24.16 ± 1.1 | 21.57 ± 1.5 | ↓ 10.76## |
| Compound 7 MD* group (250 mg/kg) | 10/10 | 24.16 ± 1.3 | 20.54 ± 2.1 | ↓ 15.15## |

*MD: Medium dose group.

Figure 9:
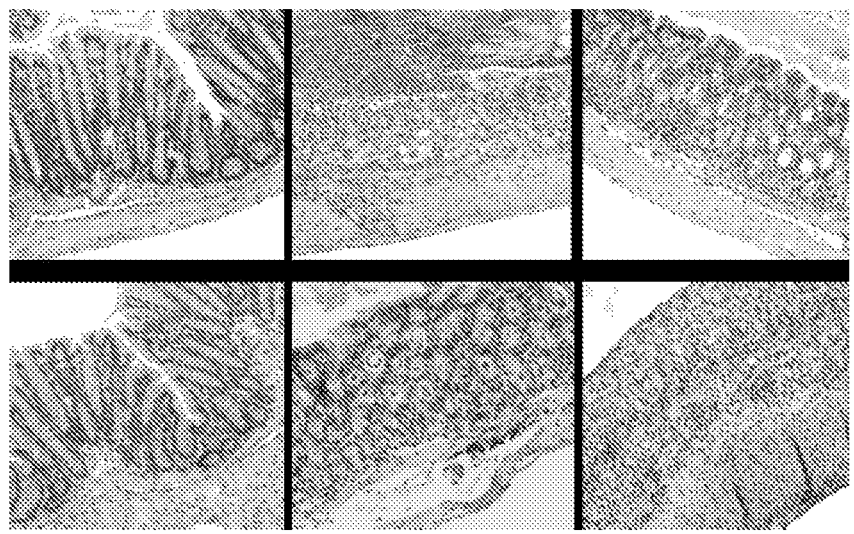
FIG. 9 shows the effect of compound 7 on the pathological change of colon tissue of C57/blc mice suffering from UC.

⑤ Compound 7 can improve the colon damage of C57/blc mice with DSS-induced UC in a dose-dependent manner (colon histopathology, HE×200) (FIG. 9).

As shown in FIG. 9, "a" represents the normal control group, "b" represents DSS model group, "c" represents positive drug SASP group, "d" represents compound 7 in HD group (500 mg/kg), "e" represents compound 7 in MD group (250 mg/kg), and "f" represents compound 7 in low dose (LD) group (125 mg/kg). Comparing with the normal control group (a), it is observed that the basic structure of intestinal epithelial cells is completely lost in the DSS model group (b) with obvious inflammatory edema, mucosa exfoliation with severe congestion and hemorrhage, infiltration of inflammatory cell into the muscular layer, and destroyed structure of muscle layer, which proves that the model is successful. Comparing with the DSS model group (b), positive drug SASP group (c) shows the improvement of visible colitis lesions and partial recovery of structure of each layer. While for the compound 7 in HD group (d), the lesion of inflammatory bowel diseases is more significantly improved, the intestinal epithelial cells arrange regularly, and the polarity arrangement of intestinal epithelial cells can even return to the normal physiological state. Moreover for the compound 7 in MD group (e) and in LD group (f), the inflammatory lesions of colon tissue also has a partial remission with a certain dose-effect relationship.

⑥ Effect of compound 7 on DAI and macroscopic score of colon tissue in C57/blc mice with DSS-induced UC (see Table 3).

DAI is evaluated by weight loss, shape of stool, hematochezia, and other indicators; macroscopic score of colon tissue is evaluated by intestinal mucosal hyperemia, edema of intestinal wall, ulcer size, and other indicators. The lower the DAI and macroscopic score is, the more close to the physiological state of the normal animal. In Table 3: **p<0.01 when compared with the normal control group; ##p<0.01 when compared with the model group.

TABLE 3

Effect of compound 7 on DAI and macroscopic score of colon tissue in C57/blc mice with DSS-induced UC

| Groups | n (start/end) | DAI | macroscopic score of colon tissue |
|---|---|---|---|
| Normal control group | 10/10 | 0.00 ± 0.00 | 0.15 ± 0.01 |
| Model group (DSS-induced) | 10/10 | 3.33 ± 0.54** | 5.54 ± 1.23** |
| SASP group (300 mg/kg) | 10/10 | 2.27 ± 0.43## | 3.24 ± 0.77## |
| Compound 7 in HD group (500 mg/kg) | 10/10 | 1.33 ± 0.31## | 2.05 ± 0.28## |
| Compound 7 in MD group (250 mg/kg) | 10/10 | 2.01 ± 0.27## | 3.30 ± 0.66## |
| Compound 7 in LD group (125 mg/kg) | 10/10 | 3.01 ± 0.38 | 4.93 ± 0.61 |

5. In vivo Test Results of Compound 1

① Compound 1 can effectively reduce the weight loss in C57/blc mice with DSS-induced UC in a good dose-dependent manner (see Table 4).

From Table 4, it is shown that compound 1 can reduce the weight loss in C57/blc mice with DSS-induced UC. In Table 4, **p<0.01 when compared with the normal control group; #p<0.05, ##p<0.01 when compared with the model group. It is not very obvious for compound 1 in HD group to inhibit the weight loss of experimental animal which is probably related with the inhibition of compound 1 to the animal appetite (data not shown). Yet, with the dosage of compound 1 gradually decreased (on the case of 75 mg/kg of dose) the experimental animals gain in body weight, even more prominent than the positive drug SASP.

TABLE 4

The therapeutic effect of compound 1 on C57/blc mice with DSS-induced acute UC in vivo

| Groups | n (start/end) | Body weight (g) x ± SD | | Change of body weight (%) |
|---|---|---|---|---|
| | | start | end | |
| Normal control group | 10/10 | 20.75 ± 1.1 | 22.25 ± 0.9 | ↑ 7.22 |
| Model group (DSS-induced) | 10/10 | 21.15 ± 1.2 | 19.80 ± 1.1 | ↓ 6.38** |
| SASP group (300 mg/kg) | 10/10 | 20.85 ± 1.4 | 21.15 ± 0.6 | ↑ 1.44## |
| Compound 1 HD group (500 mg/kg) | 10/10 | 20.07 ± 1.1 | 19.87 ± 1.0 | ↓ 1.00## |
| Compound 1 MD group (250 mg/kg) | 10/10 | 20.30 ± 1.1 | 19.95 ± 1.6 | ↓ 1.72# |
| Compound 1 LD group (75 mg/kg) | 10/10 | 20.65 ± 1.3 | 21.15 ± 1.1 | ↑ 2.42## |

Effect of compound 1 on DAI and macroscopic score of colon tissue in C57/blc mice with DSS-induced UC (see Table 5).

DAI is evaluated by weight loss, shape of stool, hematochezia, and other indicators; macroscopic score of colon tissue is calculated by intestinal mucosal hyperemia, edema of intestinal wall, ulcer size, and other indicators. The lower the DAI and macroscopic score is, the more close to the physiological state of the normal animal. In Table 5: **p<0.01 when compared with the normal control group; #p<0.05, ##p<0.01, when compared with the model group.

TABLE 5

Effect of compound 1 on DAI and macroscopic score of colon tissue in C57/blc mice with DSS-induced UC

| Groups | n (start/end) | DAI | macroscopic score of colon tissue |
|---|---|---|---|
| Normal control group | 10/10 | 0.00 ± 0.00 | 0.15 ± 0.01 |
| Model group (DSS-induced) | 10/10 | 3.39 ± 0.64** | 5.69 ± 1.12** |
| SASP group (300 mg/kg) | 10/10 | 2.54 ± 0.23## | 2.95 ± 0.52## |
| Compound 1 HD group (300 mg/kg) | 10/10 | 2.33 ± 0.11## | 2.66 ± 0.46## |
| Compound 1 MD group (150 mg/kg) | 10/10 | 1.81 ± 0.27## | 2.01 ± 0.16## |
| Compound 1 LD group (75 mg/kg) | 10/10 | 2.99 ± 0.14# | 4.93 ± 0.61 |

6. In vivo Test Results of Compound 2.

① Compound 2 can effectively reduce the weight loss in C57/blc mice with DSS-induced UC in a good dose-dependent manner (see Table 6).

As shown in table 6, it is indicated that compound 2 can effectively reduce the weight loss in C57/blc mice with DSS-induced UC at a dose of 300 mg/kg. In Table 6, **p<0.01 when compared with normal control group; ##p<0.01 when compared with the model group.

TABLE 6

The therapeutic effect of compound 2 on C57/blc mice with DSS-induced acute UC in vivo

| Groups | n (start/end) | Body weight (g) x ± SD | | Change of body weight (%) |
|---|---|---|---|---|
| | | start | end | |
| Normal control group | 10/10 | 27.22 ± 2.2 | 29.43 ± 1.6 | ↑ 8.12 |
| Model group (DSS-induced) | 10/10 | 28.60 ± 1.5 | 22.25 ± 1.8 | ↓ 22.22** |
| SASP group (300 mg/kg) | 10/10 | 27.89 ± 2.5 | 25.09 ± 0.9 | ↓ 12.09## |
| Compound 2 group (300 mg/kg) | 10/10 | 28.56 ± 1.2 | 26.17 ± 1.5 | ↓ 8.37## |

Effect of compound 2 on DAI and macroscopic score of colon tissue in C57/blc mice with DSS-induced UC (see Table 7).

DAI is evaluated by weight loss, shape of stool, hematochezia, and other indicators; macroscopic score of colon tissue is evaluated by intestinal mucosal hyperemia, edema of intestinal wall, ulcer size, and other indicators. The lower the DAI and macroscopic score is, the more close to the physiological state of the normal animal. DAI: Disease activity index; in Table 7: **p<0.01 when compared with the normal control group; ##p<0.01 when compared with the model group. Compound 2 can effectively alleviate the loose stools, hematochezia, and other symptoms of subjects at the dosage of 300 mg/kg, and shows more prominent efficacy than the positive drug SASP.

TABLE 7

Effect of compound 2 on DAI and macroscopic score of colon tissue in C57/blc mice with DSS-induced UC

| Groups | n (start/end) | DAI | macroscopic score of colon tissue |
|---|---|---|---|
| Normal control group | 10/10 | 0.00 ± 0.00 | 0.10 ± 0.01 |
| Model group (DSS-induced) | 10/10 | 3.85 ± 0.34** | 5.59 ± 1.01** |
| SASP group (300 mg/kg) | 10/10 | 2.27 ± 0.43## | 3.24 ± 0.77## |
| Compound 2 group (300 mg/kg) | 10/10 | 1.05 ± 0.26## | 2.94 ± 0.21## |

What is claimed is:

1. Protoberberine alkaloid derivative of general formula (I) or a pharmaceutically acceptable salt thereof:

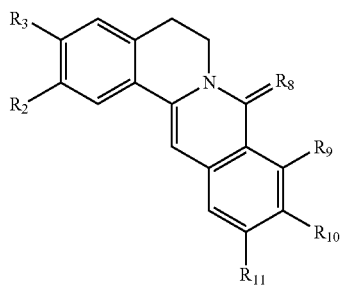

I wherein:
≡≡≡ represents a single bond;
$R_8$ represents H; and wherein
when $R_2$ and $R_3$ independently represents $OCH_3$,
$R_9$ and $R_{10}$ independently represents $OCH_3$ and $R_{11}$ represents H, or $R_9$ and $R_{10}$ form a $OCH_2O$ together and $R_{11}$ represents H, or $R_{10}$ and $R_{11}$ form a $OCH_2O$ together and $R_9$ represents H; or
when $R_2$ and $R_3$ form a $OCH_2O$ together
$R_9$ and $R_{10}$ form a $OCH_2O$ together and $R_{11}$ represents H, or $R_{10}$ and $R_{11}$ form a $OCH_2O$ together and $R_9$ represents H.

2. Protoberberine alkaloid derivative or a pharmaceutically acceptable salt thereof, selected from the group consisting of:

1

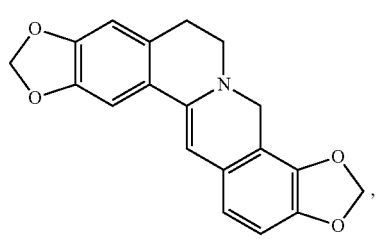

2

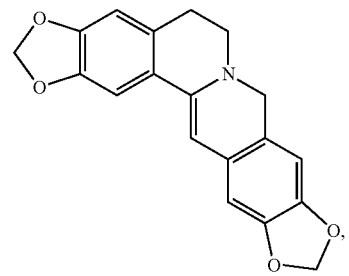

4

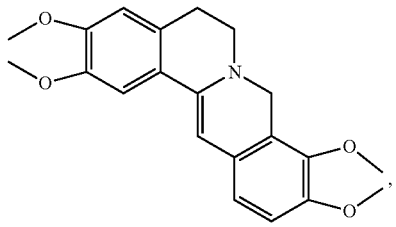

5

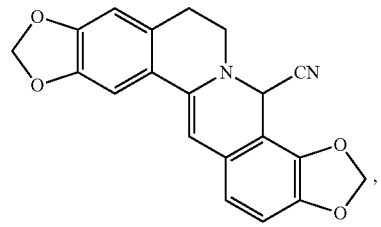

6

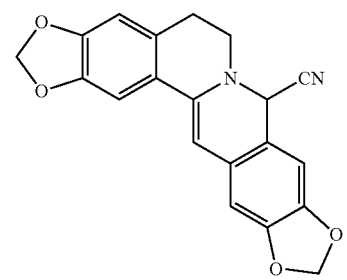

7

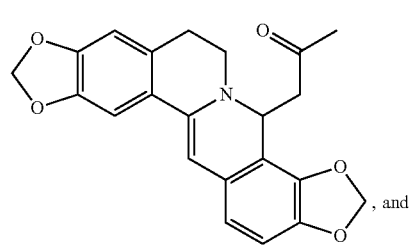

, and

8

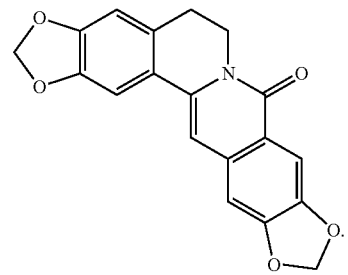

3. A pharmaceutical composition comprising effective amount of the derivative or pharmaceutically acceptable salt thereof, according to claim 1 or 2, and one or more common pharmaceutically acceptable carriers.

4. A method for treating ulcerative colitis in a subject in need thereof, comprising administrating to the subject an effective amount of the protoberberine alkaloid derivative or pharmaceutically acceptable salt thereof, according to claim 1 or 2, or the pharmaceutically composition of claim 3.

5. A method for treating ulcerative colitis in a subject in need thereof, comprising administrating to the subject an effective amount of compound 3 or compound 9, having the following formula:

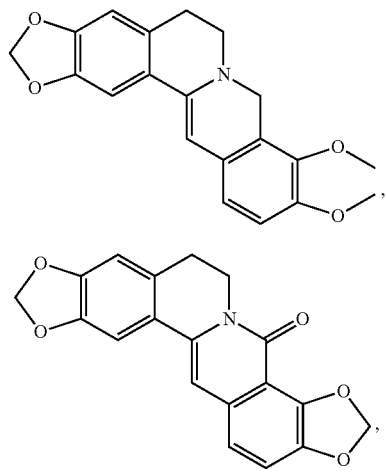

respectively, or a pharmaceutically acceptable salt thereof.

6. Protoberberine alkaloid derivative or a pharmaceutically acceptable salt thereof of general formula (I):

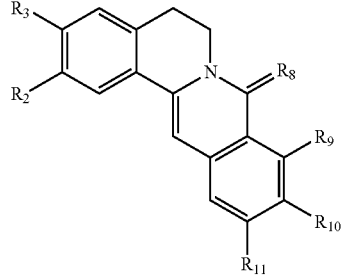

I wherein:
 ═══ represents a a double bond;
 $R_8$ represents 0; and wherein
 when $R_2$ and $R_3$ independently represent $OCH_3$,
  $R_9$ and $R_{10}$ independently represents $OCH_3$ and $R_{11}$ represents H, or $R_9$ and $R_{10}$ form a $OCH_2O$ together and $R_{11}$ represents H, or $R_{10}$ and $R_{11}$ form a $OCH_2O$ together and $R_9$ represents H; or
 when $R_2$ and $R_3$ form a $OCH_2O$ together
  $R_{10}$ and $R_{11}$ form a $OCH_2O$ together and $R_9$ represents H.

7. A method for treating ulcerative colitis in a subject in need thereof, comprising administrating to the subject an effective amount of a derivative or a pharmaceutically acceptable salt thereof, according to claim 6.

* * * * *